(12) United States Patent
Furukawa et al.

(10) Patent No.: US 10,090,132 B2
(45) Date of Patent: Oct. 2, 2018

(54) CHARGED PARTICLE BEAM IRRADIATION APPARATUS

(71) Applicants: NATIONAL INSTITUTES FOR QUANTUM AND RADIOLOGICAL SCIENCE AND TECHNOLOGY, Chiba-shi (JP); TOSHIBA ENERGY SYSTEMS & SOLUTIONS CORPORATION, Kawasaki-shi (JP)

(72) Inventors: Takuji Furukawa, Chiba (JP); Shigeki Takayama, Yokohama (JP); Takashi Yazawa, Ota (JP); Yoshiharu Kanai, Yokohama (JP); Kosuke Sato, Kamakura (JP); Tomofumi Orikasa, Yokohama (JP); Kei Koyanagi, Yokohama (JP)

(73) Assignees: NATIONAL INSTITUTES FOR QUANTUM AND RADIOLOGICAL SCIENCE AND TECHNOLOGY, Chiba-shi (JP); TOSHIBA ENERGY SYSTEMS & SOLUTIONS CORPORATION, Kawasaki-shi (JP)

( * ) Notice: Subject to any disclaimer, the term of this patent is extended or adjusted under 35 U.S.C. 154(b) by 0 days.

(21) Appl. No.: 15/497,831

(22) Filed: Apr. 26, 2017

(65) Prior Publication Data
US 2017/0229281 A1    Aug. 10, 2017

Related U.S. Application Data

(63) Continuation of application No. PCT/JP2015/077711, filed on Sep. 30, 2015.

(30) Foreign Application Priority Data

Oct. 28, 2014  (JP) .................................. 2014-219305
Jun. 10, 2015  (JP) .................................. 2015-117703

(51) Int. Cl.
*H01J 37/147*  (2006.01)
*A61N 5/10*  (2006.01)

(52) U.S. Cl.
CPC ........ *H01J 37/1475* (2013.01); *A61N 5/1077* (2013.01); *H01J 2237/04922* (2013.01)

(58) Field of Classification Search
USPC .................................................. 250/396 ML
See application file for complete search history.

(56) References Cited

U.S. PATENT DOCUMENTS 2,213,172 A * 8/1940 Sherman ................. H01J 29/74
                                                        313/427
2,803,781 A * 8/1957 Jurgens .................... H01J 29/70
                                                        313/429

(Continued)

FOREIGN PATENT DOCUMENTS

JP    5-264797     10/1993
JP    2007-260222   10/2007

(Continued)

OTHER PUBLICATIONS

International Search Report dated Dec. 28, 2015 in PCT/JP2015/077711, filed on Sep. 30, 2015.

*Primary Examiner* — Phillip A Johnston
(74) *Attorney, Agent, or Firm* — Oblon, McClelland, Maier & Neustadt, L.L.P.

(57) ABSTRACT

A charged particle beam irradiation apparatus according to an embodiment includes: a first scanning electromagnet device configured to deflect a charged particle beam to a second direction that is substantially perpendicular to a first direction along which the charged particle beam enters, the first scanning electromagnet device having an aperture on an outlet side larger than that on an inlet side; and a second scanning electromagnet device configured to deflect the charged particle beam to a third direction that is substantially (Continued)

perpendicular to the first direction and the second direction, the second scanning electromagnet device having an aperture on an outlet side larger than that on an inlet side, the first scanning electromagnet device and the second scanning electromagnet device being disposed to be parallel with the first direction.

20 Claims, 20 Drawing Sheets

(56) References Cited

U.S. PATENT DOCUMENTS

| | | | | |
|---|---|---|---|---|
| 4,587,504 A | * | 5/1986 | Brown | G01R 33/3815 324/319 |
| 5,221,836 A | * | 6/1993 | Kinoshita | H01J 31/502 250/214 VT |
| 5,393,984 A | * | 2/1995 | Glavish | G21K 1/093 250/396 ML |
| 5,719,402 A | * | 2/1998 | Satoh | B82Y 10/00 250/396 ML |
| 7,498,572 B2 | * | 3/2009 | Fujita | H01J 37/1475 250/294 |
| 8,071,955 B2 | * | 12/2011 | Kim | H01J 37/147 250/396 ML |
| 8,222,617 B2 | | 7/2012 | Iseki et al. | |
| 9,368,315 B2 | * | 6/2016 | Kinoshita | G01J 11/00 |
| 2009/0101832 A1 | | 4/2009 | Diehl | |
| 2013/0043403 A1 | | 2/2013 | Gordon et al. | |

FOREIGN PATENT DOCUMENTS

| | | |
|---|---|---|
| JP | 2010-125012 A | 6/2010 |
| JP | 2011-72717 | 4/2011 |
| JP | 2013-96949 | 5/2013 |
| WO | WO 2015/045017 A1 | 4/2015 |

* cited by examiner

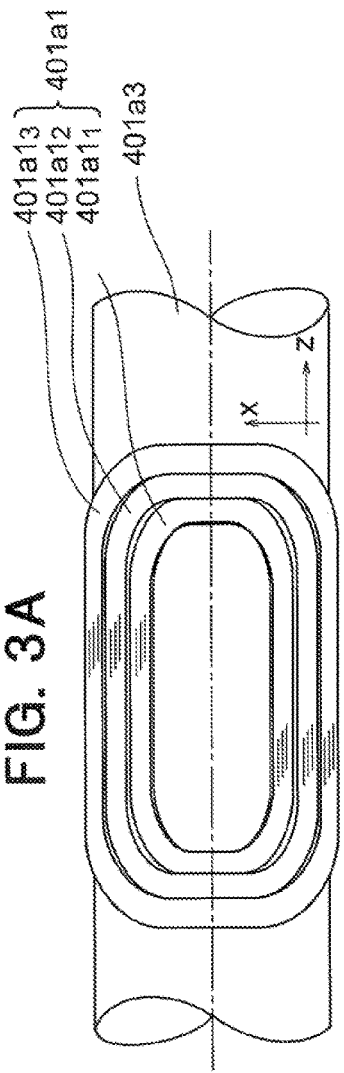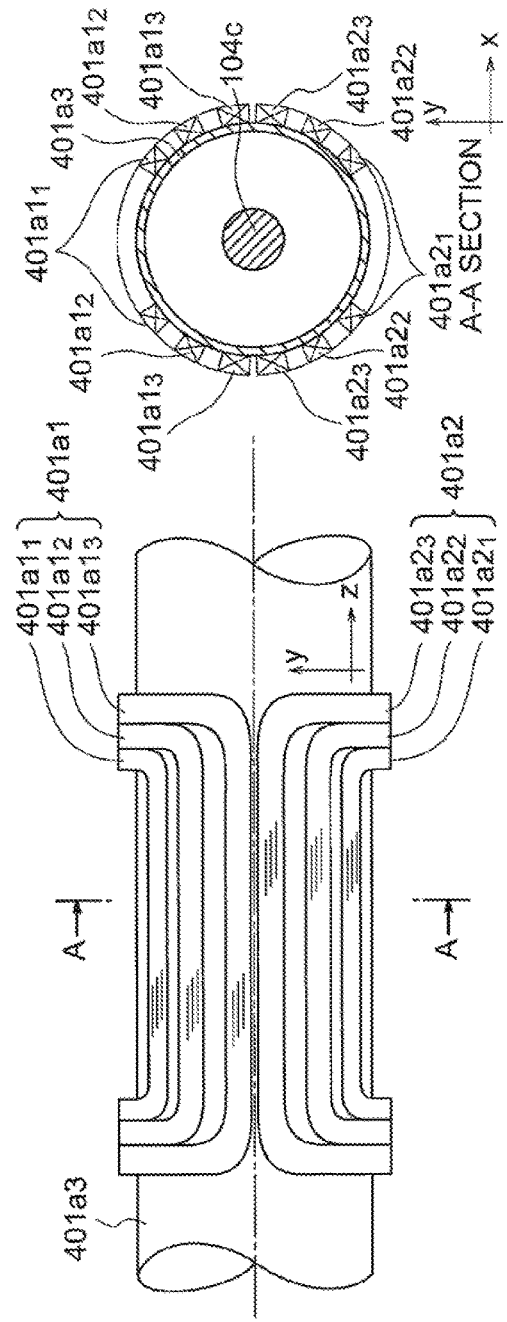

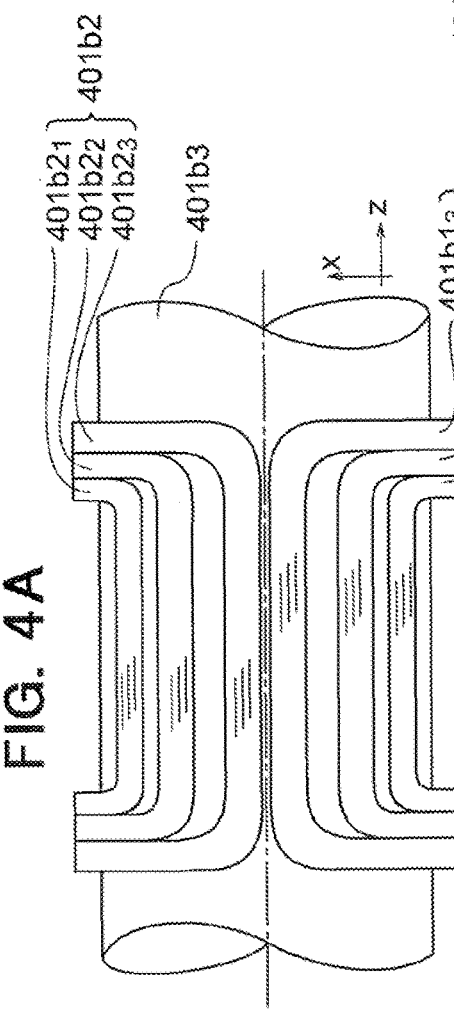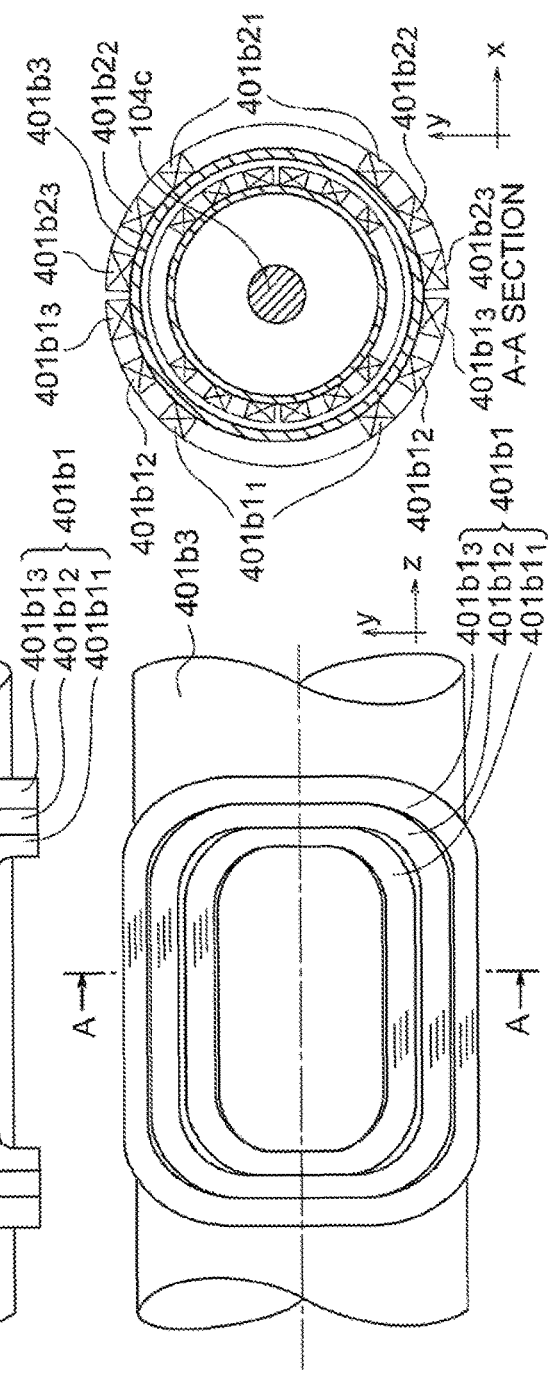

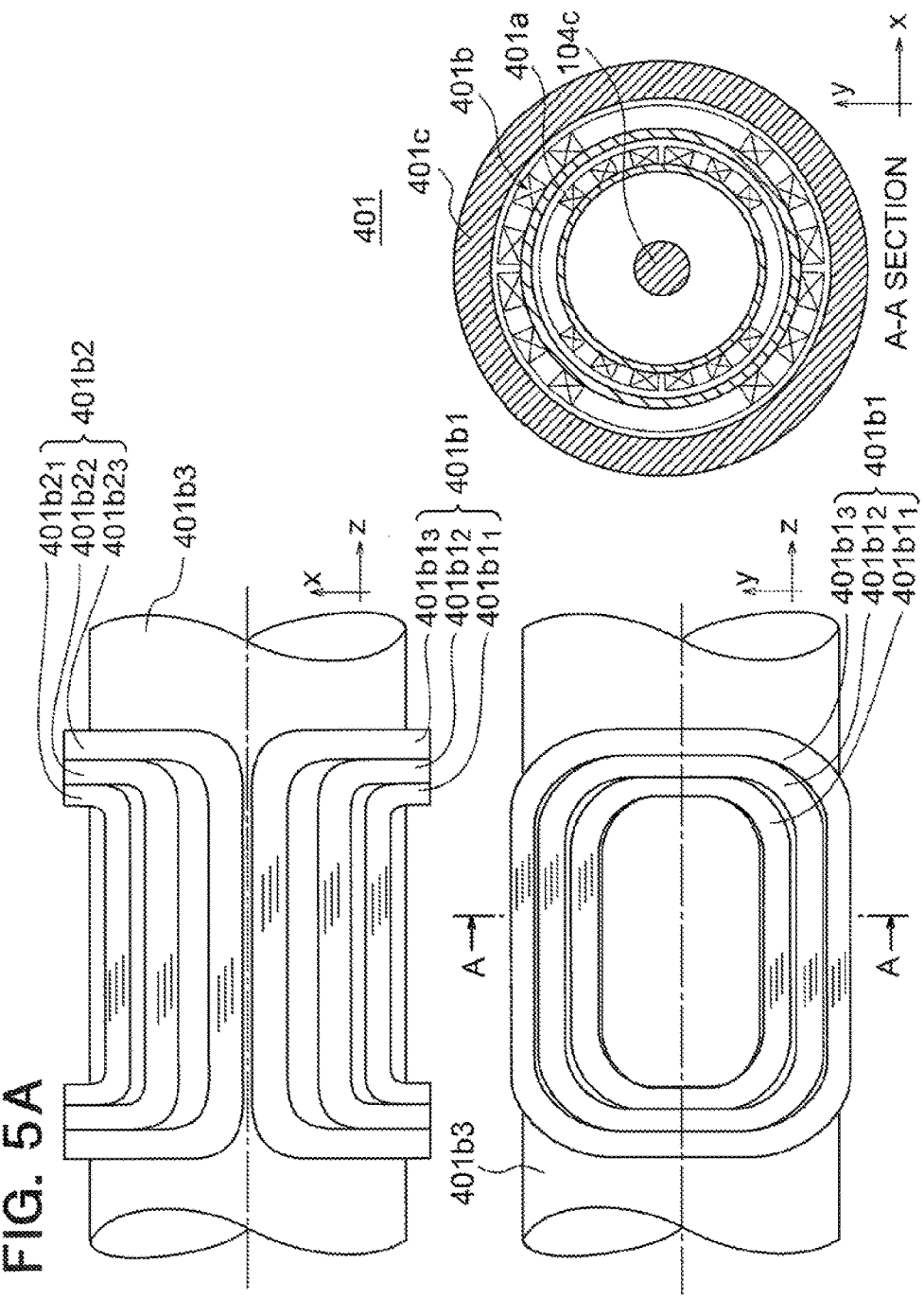

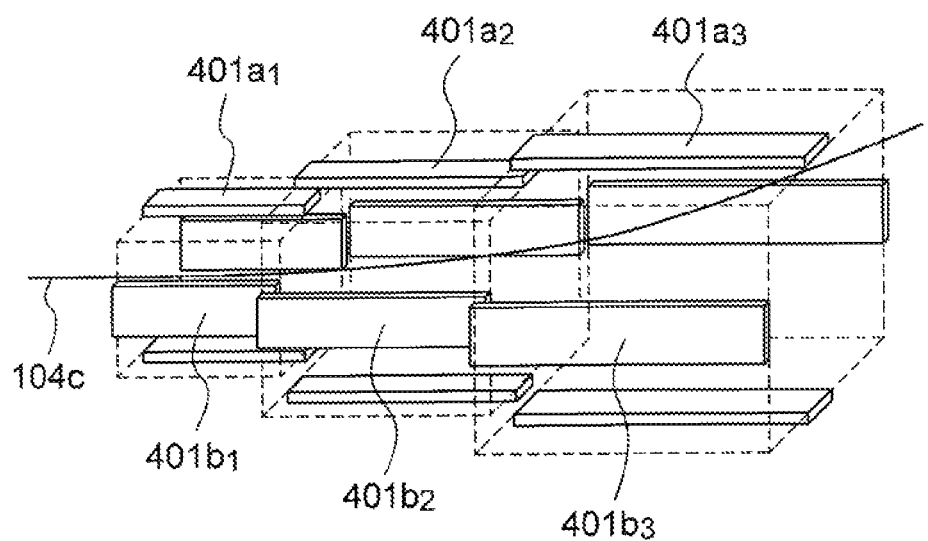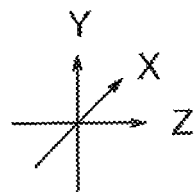
FIG. 6

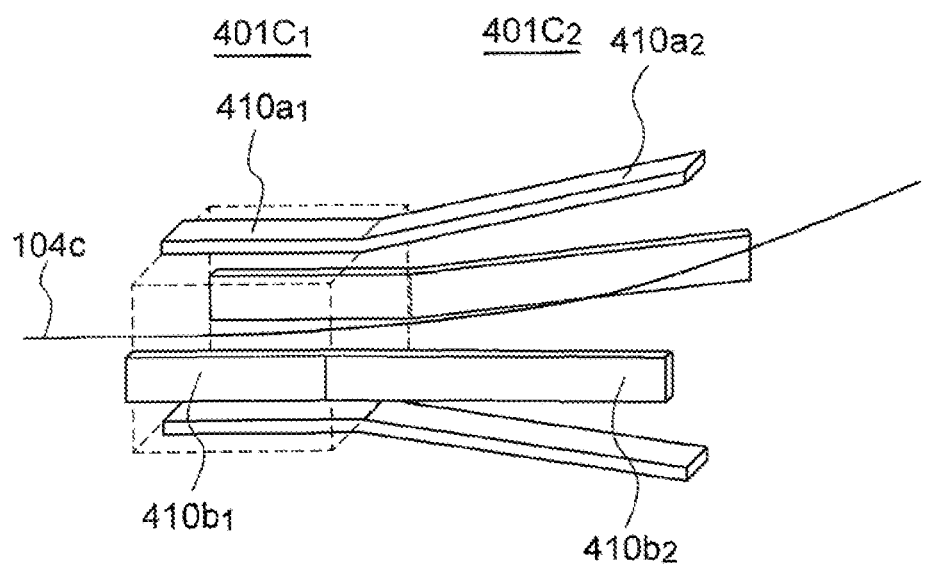
FIG. 9
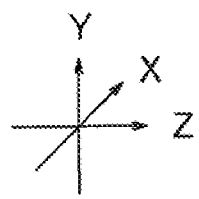

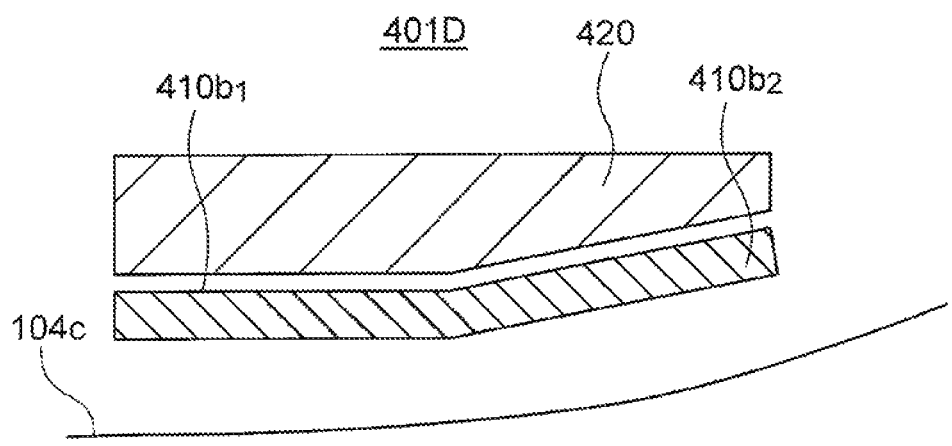
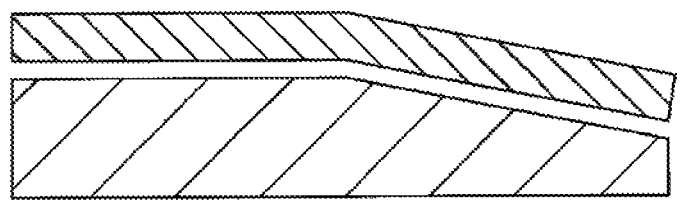
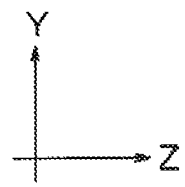
FIG. 18

CHARGED PARTICLE BEAM IRRADIATION APPARATUS

CROSS REFERENCE TO RELATED APPLICATIONS

This application is a continuation of International Application No. PCT/JP2015/077711, filed on Sep. 30, 2015, which is based upon and claims the benefit of priority from the prior Japanese Patent Applications No. 2014-219305, filed on Oct. 28, 2014, and No. 2015-117703, filed on Jun. 10, 2015, the entire contents of which are incorporated herein by reference.

FIELD

Embodiments described herein relate to charged particle beam irradiation apparatuses.

BACKGROUND

Charged particle beam irradiation apparatuses are known, which emit a charged particle beam such as a heavy particle beam to a diseased part of a patient with a cancer or the like. A charged particle beam irradiation apparatus is an apparatus which generates a charged particle beam at a beam generation device, accelerates the charged particle beam at a beam acceleration device, transports the accelerated charged particle beam through a beam transport device, and emits the accelerated charged particle beam from a beam irradiation device to the diseased part in a treatment room. The beam irradiation device emits the beam in accordance with a three-dimensional shape of the target diseased part. The beam irradiation device includes two pairs of scanning electromagnets, for example a pair of horizontally scanning electromagnets and a pair of vertically scanning electromagnets arranged in series, and scans charged particle beams in two directions that are perpendicular to each other.

In order to emit beams to cancers in various body parts and with various sizes, the range of irradiation (irradiation field) is preferably as broad as possible. Roughly speaking, there are two ways for broadening the irradiation field. First, series-connected two pairs of scanning electromagnets are located at a great distance from the patient to whom the charged particle beams are emitted. Second, the magnetic field strength of the outputs from the two pairs of scanning electromagnets is increased, or the axis length is elongated.

If the series-connected two pairs of scanning electromagnets are located at a great distance from the patient in order to secure a broad irradiation field, a great space is needed to install the charged particle beam irradiation apparatus. Therefore, a large housing may be needed for the apparatus.

On the other hand, if the magnetic field strength of the outputs from the scanning electromagnets is increased, or the axis length is elongated, the magnetic field generation efficiency of the scanning electromagnets downstream in the beam movement direction is lowered. Therefore, the irradiation field may not be sufficiently obtained.

BRIEF DESCRIPTION OF THE DRAWINGS

FIGS. 3A to 3C are explanatory diagrams of vertical scanning electromagnets according to the first embodiment.

FIGS. 4A to 4C are explanatory diagrams of horizontal scanning electromagnets according to the first embodiment.

FIGS. 5A to 5C are explanatory diagrams of scanning electromagnets according to a modification of the first embodiment.

FIG. 6 is a diagram showing scanning electromagnets included in a charged particle beam irradiation apparatus according to a second embodiment.

FIG. 9 is a drawing showing scanning electromagnets included in a charged particle beam irradiation apparatus according to a fourth embodiment.

FIG. 18 is a diagram showing a scanning electromagnet included in a charged particle beam irradiation apparatus according to an eighth embodiment.

DETAILED DESCRIPTION

A charged particle beam irradiation apparatus according to an embodiment includes: a first scanning electromagnet device configured to deflect a charged particle beam to a second direction that is substantially perpendicular to a first direction along which the charged particle beam enters, the first scanning electromagnet device having an aperture on an outlet side larger than that on an inlet side; and a second scanning electromagnet device configured to deflect the charged particle beam to a third direction that is substantially perpendicular to the first direction and the second direction, the second scanning electromagnet device having an aperture on an outlet side larger than that on an inlet side, the first scanning electromagnet device and the second scanning electromagnet device being disposed to be parallel with the first direction.

Embodiments of a charged particle beam irradiation apparatus will now be described with reference to the accompanying drawings.

First Embodiment

Figure 1:
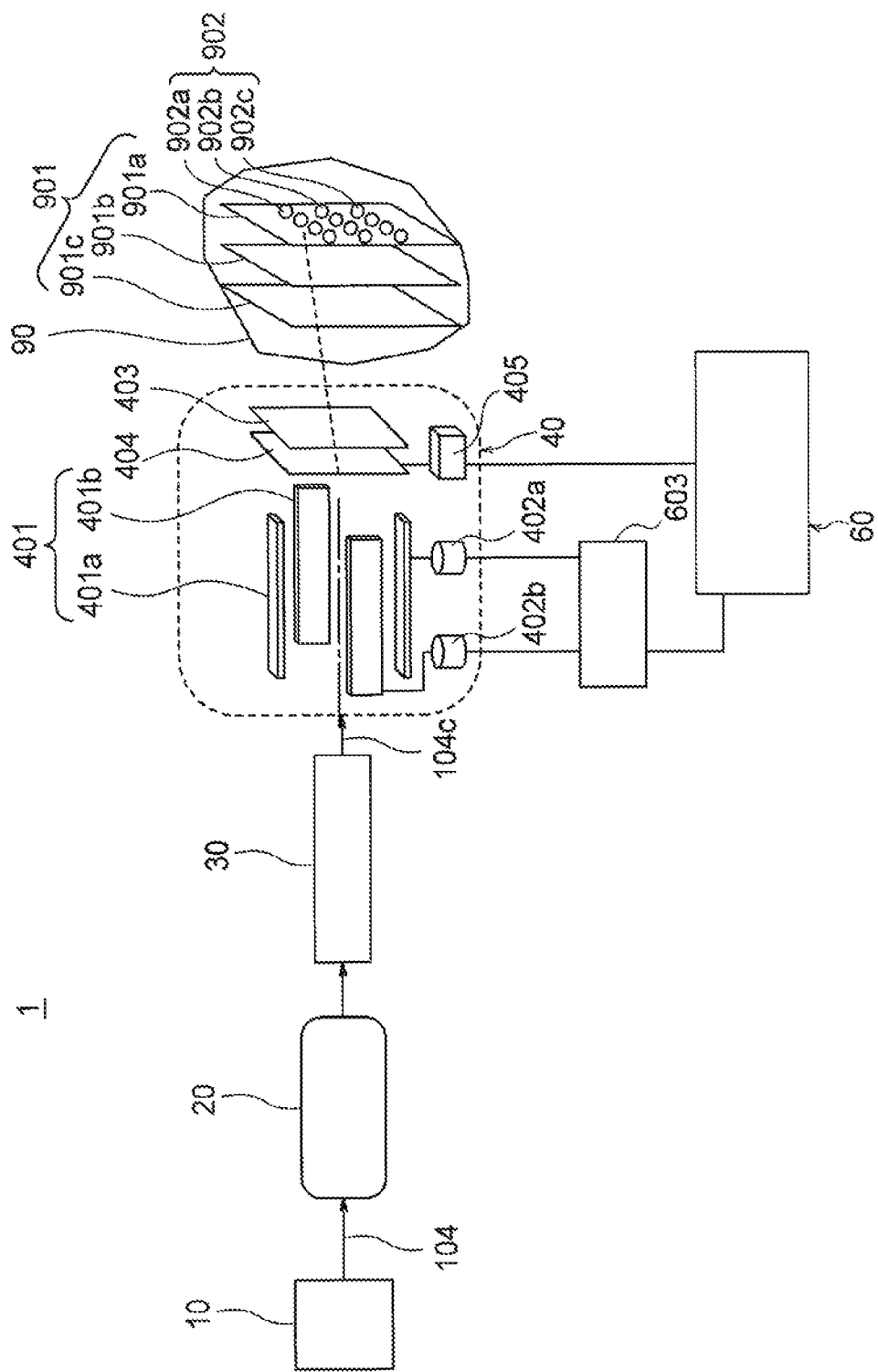
FIG. 1 is a diagram showing a charged particle beam irradiation apparatus according to a first embodiment.

FIG. 1 shows a charged particle beam irradiation apparatus according to a first embodiment. The charged particle beam irradiation apparatus 1 according to this embodiment is an irradiation apparatus 1 including a particle beam source of charged particles, for example negative pions, protons, helium ions, carbon ions, neon ions, silicon ions, or argon ions to perform a radiation therapy.

As shown in FIG. 1, the charged particle beam irradiation apparatus 1 includes a beam generation device 10, a beam acceleration device 20, a beam transport device 30, a beam irradiation device 40, and an irradiation control device 60, and emits a charged particle beam 104 to, for example, a diseased part 90 of a patient.

The beam generation device 10 generates charged particle beams.

The beam acceleration device 20 is a device for accelerating the charged particle beam 104 to a predefined energy. The beams acceleration device 20 has a structure including, for example, a former-part accelerator and a latter-part accelerator. For example, the former-part accelerator includes a linear accelerator, and the latter-part accelerator includes a synchrotron. Such components as a vacuum chamber (pipe), a high-frequency acceleration cavity, a beam deflector (dipole electromagnet), a beam converging/diverging device (quadrupole electromagnet), a beam trajectory corrector (electromagnetic steering), a reception device, an emission device, and a control device are included as constituent elements. The structure of the beam acceleration device 20 may be arbitrarily determined. Therefore, the structure is not described in detail. A cyclotron or the like may be selected as the accelerator.

The beam transport device 30 is a device to transport the accelerated charged particle beam 104 to a target, namely the diseased part 90 of the patient in the irradiation treatment room. The constituent elements of the beam transport device 30 include a vacuum chamber (pipe), a beam deflector (dipole electromagnet), a beam converging/diverging device (quadrupole electromagnet), a beam trajectory corrector (electromagnetic steering), and a control device.

The beam irradiation device 40 is disposed on the charged particle beam outlet side of the beam transport device 30, and adjusts the trajectory of a charged particle beam 104c having a specific energy that has passed the beam transport device 30, so that the charged particle beam 104c accurately enters a set irradiation point 902 of the diseased part 90 of the patient. The beam irradiation device 40 also monitors the irradiation position and the irradiation dose of the charged particle beam 104c at the diseased part 90. Included in the beam irradiation device 40 are a scanning electromagnet 401, a scanning electromagnet power supply 402, a position monitor 403, a dosimeter 404, and a dosimeter circuit 405.

The scanning electromagnet 401 is controlled by an excitation current, and includes a pair of vertical scanning electromagnets 401a for adjusting the trajectory in the vertical direction of the charged particle beam 104c, and a pair of horizontal scanning electromagnets 401b for adjusting the trajectory in the horizontal direction of the charged particle beam 104c. The scanning electromagnet power supply 402 includes electromagnet power supplies 402a and 402b. The electromagnet power supply 402a supplies the scanning electromagnets 401a with an excitation current needed for the scanning of the charged particle beam 104c. The electromagnet power supply 402b supplies the scanning electromagnets 401b with an excitation current needed for the scanning of the charged particle beam 104c. The pair of vertical scanning electromagnets 401a and the pair of horizontal scanning electromagnets 401b will be described in more detail later.

The position monitor 403 outputs a signal indicative of a position of the charged particle beam 104c passing through the position monitor 403, namely a position at which the charged particle beam enters the diseased part 90 of the patient, and sends the signal to the irradiation control device 60. The position monitor 403 may be of an ionization chamber type.

The dosimeter 404 outputs an electrical signal according to the intensity or dose of the charged particle beam 104c passing through the dosimeter 404, namely the intensity or dose of the charged particle beam emitted to the diseased part 90 of the patient. The dosimeter 404 may be of an ionization chamber type.

The dosimeter circuit 405 receives the electrical signal outputted from the dosimeter 404, and, when the received electrical signal reaches a preset integration output value, sends to the irradiation control device 60 a dose complete signal indicating that a preset dose is applied to a predefined irradiation point 902 of the diseased part 90 of the patient.

The irradiation control device 60 is configured to be capable of recording irradiation pattern data indicating how the radiation therapy is performed on the patient, and controls the whole of the charged particle beam irradiation apparatus 1 by referring to the irradiation pattern data. The irradiation pattern data is generated from optimum irradiation information prepared in a therapy plan before performing the radiation therapy.

The irradiation pattern data includes the horizontal relative position and the vertical relative position relative to a reference position serving as a position indicator of the irradiation point 902, set for each of irradiation slices 901 that are virtually cut from the diseased part 90 of the patient, the range in the patient's body serving as an indicator of the position of an irradiation slice 901, namely an indicator of a depth in the patient's body, the beam stop width serving as an indicator of the beam stop width in the patient's body, the beam intensity and the set dose of a beam to be emitted to each irradiation point 902. Thus, the irradiation pattern data includes all the information needed to control part of or entire operation of the beam generation device 10, the beam acceleration device 20, the beam transport device 30, and the beam irradiation device 40. The beam stop width is resulted from a difference in the range in the patient's body caused by the energy width of the charged particle beam. The contents of the irradiation pattern data may be arbitrarily changed.

The irradiation control device 60 includes a beam convergence control unit 601, an energy selection control unit 602, and a scan control unit 603.

The scan control unit 603 controls the output of the scanning electromagnet power supply 402 so that the charged particle beam 104c enters a predefined irradiation point 902, thereby adjusting the excitation current applied to the scanning electromagnet 401.

(Vertical Scanning Electromagnets and Horizontal Scanning Electromagnets)

Figure 2:
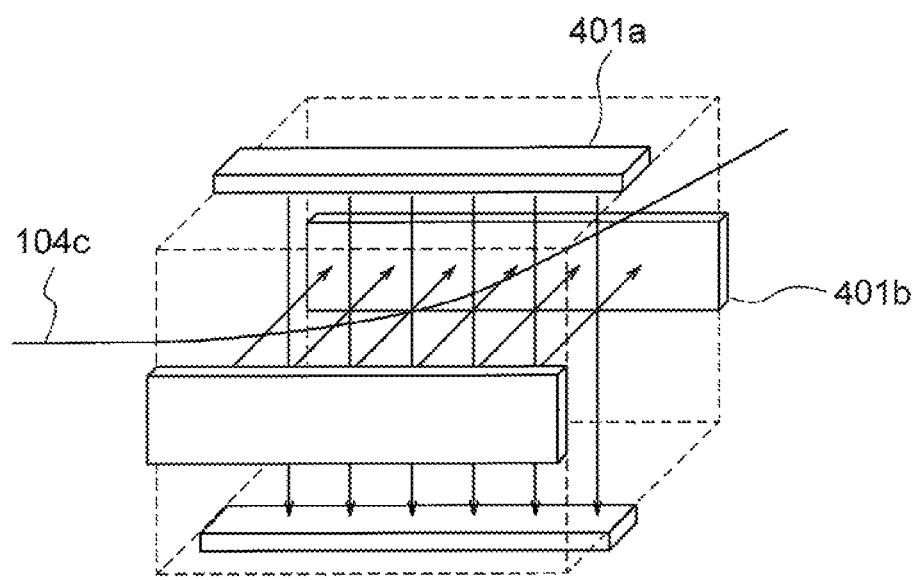
FIG. 2 is an explanatory diagram of scanning electromagnets used in the first embodiment.

Next, the vertical scanning electromagnets and the horizontal scanning electromagnets will be described in detail. The pair of vertical scanning electromagnets 401a and the pair of horizontal scanning electromagnets 401b are arranged so as to be parallel with the moving direction of the charged particle beam 104c, as shown in FIG. 2. The pair of vertical scanning electromagnets 401a is arranged in the vertical direction, and the pair of horizontal scanning electromagnets 401b is arranged in the horizontal direction at locations corresponding to locations of the pair of vertical scanning electromagnets 401a. The pair of vertical scanning electromagnets 401a and the pair of horizontal scanning electromagnets 401b are arranged to perform scanning simultaneously in two directions that are perpendicular to each other, namely the vertical direction and the horizontal direction.

The details of the pair of vertical scanning electromagnets 401a will be described with reference to FIGS. 3A to 3C. FIG. 3A is a top view of the pair of vertical scanning electromagnets 401a, FIG. 3B is a side view of the pair of vertical scanning electromagnets 401a, and FIG. 3C is a cross-sectional view taken along line A-A of FIG. 3B.

The pair of vertical scanning electromagnets 401a includes a hollow structure 401a3, a coil device 401a1 disposed on the upper surface of the structure 401a3, and a coil device 401a2 disposed on the lower surface of the structure 401a3. The structure 401a3 is formed of a material that does not cause an eddy current, for example, a non-magnetic metal or a fiber-reinforced plastic (FRP).

The coil device 401a1 includes a coil $401a1_1$ having a saddle-like shape and disposed on the upper surface of the structure 401a3, a coil $401a1_2$ disposed outside the coil $401a1_1$, and a coil $401a1_3$ disposed outside the coil $401a1_2$. The coils $401a1_1$, $401a1_2$, and $401a1_3$ are coated with an insulating material.

The coil device 401a2 includes a coil $401a2_1$ having a saddle-like shape and disposed on the lower surface of the structure 401a3, a coil $401a2_2$ disposed outside the coil $401a1_1$, and a coil $401a2_3$ disposed outside the coil $401a2_2$. The coils $401a2_1$, $401a2_2$, and $401a2_3$ are coated with an insulating material. A magnetic field is generated in the vertical direction by causing an excitation current to flow through the coils $401a1_1$ to $401a1_3$ and $401a2_1$ to $401a2_3$. Although three coils each are disposed on the upper side and the lower side in FIGS. 3A to 3C, the number of coils may be one, two, or four or more. In FIG. 3C, the reference numeral 104c denotes a charged particle beam.

The details of the pair of horizontal scanning electromagnets 401b will be described with reference to FIGS. 4A to 4C. FIG. 4A is a top view of the pair of horizontal scanning electromagnets 401b, FIG. 4B is a side view of the pair of horizontal scanning electromagnets 401b, and FIG. 4C is a cross-sectional view taken along A-A in FIG. 4B.

The pair of horizontal scanning electromagnets 401b includes a hollow structure 401b3 disposed outside the pair of vertical scanning electromagnets 401a, a coil device 401b1 disposed on one of side surface of structure 401b3, and a coil device 401b2 disposed on the other of the side surfaces of the structure 401b3. Like the structure 401a3, the structure 401b3 is formed of a material that does not cause an eddy current, for example, a nonmagnetic metal or a fiber-reinforced plastic (FRP). The horizontal scanning electromagnets 401b may be disposed inside the vertical scanning electromagnets 401a.

The coil device 401b1 includes a coil $401b1_1$ having a saddle-like shape and disposed on the one of the side surfaces of the structure 401a3, a coil $401b1_2$ disposed outside the coil $401b1_1$, and a coil $401b1_3$ disposed outside the coil $401b1_2$. The coils $401b1_1$, $401b1_2$, and $401b1_3$ are coated with an insulating material.

The coil device 401b2 includes a coil $401b2_1$ having a saddle-like shape and disposed on the other of the side surfaces of the structure 401a3, a coil $401b2_2$ disposed outside the coil $401b2_1$, and a coil $401b2_3$ disposed outside the coil $401b2_2$. The coils $401b2_1$, $401b2_2$, and $401b2_3$ are coated with an insulating material. A magnetic field is generated in the horizontal direction by causing an excitation current to flow through the coils $401b1_1$ to $401b1_3$ and $401b2_1$ to $401b2_3$. Although three coils each are disposed on the pair of side surfaces in FIGS. 4A to 4C, the number of coils may be one, two, or four or more. In FIG. 4C, the reference numeral 104c denotes a charged particle beam.

In this embodiment, a yoke 401c is preferably disposed outside the horizontal scanning electromagnets 401b as shown in FIGS. 5A to 5C. FIG. 5A is a top view of the scanning electromagnet 401 without the yoke 401c, FIG. 5B is a side view of the scanning electromagnet 401 without the yoke 401c, and FIG. 5C is a cross-sectional view taken along line A-A of FIG. 5B. The presence of the yoke 401c may prevent the magnetic field from leaking outside. In FIG. 5C, the reference numeral 104c denotes a charged particle beam.

(Operation of Charged Particle Beam Irradiation Apparatus 1)

Next, the operation of the charged particle beam irradiation apparatus 1 will be described.

The descriptions of the operation below are based on an example in which a radiation therapy is performed by using a so-called spot scanning irradiation method. The spot scanning irradiation method has been established in the field of accelerator-driven particle beam irradiation technology, and has been proven to have a high therapeutic effect.

In the spot scanning irradiation method, the diseased part of the patient is virtually divided into three-dimensional grid points, namely irradiation slices and irradiation points set on the irradiation slices, and scanned in the depth direction of the diseased part (the direction along the charged particle beam axis) and in the sectional direction of the diseased part (the direction crossing the charged particle beam axis) with charged particle beams.

Irradiation of one irradiation point with the charged particle beam is suspended when a dose complete signal is generated, indicating that the dose to the irradiation point reaches a set dose amount. Thereafter, the charged particle beam is moved to another irradiation point or irradiation slice and irradiation is restarted. The entire diseased part is irradiated by repeating this operation.

It is assumed, for example, that each of slice surfaces 901a to 901c has irradiation spots (in the drawing, irradiation points 902 on the slice surface 901a). First, the devices are adjusted in accordance with a set irradiation spot. The slice surface may be changed by changing the energy of the beam. As the energy becomes higher, the point reached by the beam becomes deeper (in FIG. 1, the slice surface 901a), and as the energy becomes lower, the point reached by the beam becomes shallower (in FIG. 1, the slice surface 901c). The energy of the beam may be changed by reducing the energy of the accelerated beam at the beam acceleration device 20, or appropriately filtering the beam accelerated at the beam acceleration device 20 by means of the beam transport device 30 or the beam irradiation device 40.

The excitation amount of the electromagnets included in the beam transport device 30 is also adjusted based on the selection of the energy of the charged particle beam. This ensures the required intensity of the charged particle beam arriving at the diseased part 90 of the patient.

The excitation current of the scanning electromagnet 401 in the beam irradiation device 40 is adjusted and set so that a charged particle beam with a predefined amount of energy correctly hits the irradiation point (for example, the irradiation point 902a).

After the devices are adjusted as described above, the charged particle beam 104 is emitted from the beam generation device 10 under the control of the irradiation control device 60.

The charged particle beam 104 emitted from the beam generation device 10 is accelerated at the beam acceleration device 20, and guided to the beam transport device 30. At the beam transport device 30, the charged particle beam 104 enters a magnetic field formed by, for example, a beam deflector (not shown), by which the trajectory of the charged particle beam 104 is deflected according to its momentum. As a result, the charged particle beam 104 is stably guided to the beam irradiation device 40. At the beam irradiation device 40, the charged particle beam 104c enters a magnetic field formed by the scanning electromagnet 401, by which the horizontal trajectory and the vertical trajectory are adjusted. Thereafter, the charged particle beam 104c moves toward the irradiation point on each slice surface (in the example of the irradiation slice 901a, the set irradiation point 902a), to perform the radiation therapy on the irradiation point 902a.

The irradiation control device 60 monitors whether the charged particle beam 104c with the trajectory adjusted based on the output signal from the position monitor 403 correctly hits the irradiation point 902a.

The irradiation point 902a is continuously irradiated with the charged particle beam until the dose complete signal is outputted from the dosimeter circuit 405. When the dose complete signal is outputted, and inputted to the irradiation control device 60, the irradiation is moved to another irradiation point (for example, the irradiation point 902b). Specifically, the irradiation control device 60 refers to the irradiation pattern data, the excitation current of the scanning electromagnet 401 is adjusted so that the irradiation point 902b is irradiated with the charged particle beam, and the irradiation of the irradiation point 902b with the charged particle beam continues until a dose complete signal is inputted to the irradiation control device 60 again. This operation is repeated to irradiate all the irradiation points 902 set on the irradiation slice 901a.

After the irradiation of the irradiation slice 901a is completed, irradiation of another irradiation slice 901b starts. Specifically, the irradiation control device 60 refers to the irradiation pattern data, adjusts the beam acceleration device 20 so that the charged particle beam converges at the location of the irradiation slice 901b, and adjusts the beam irradiation device 40 so that the charged particle beam hits the respective irradiation points (not shown) on the irradiation slice 901b. The operation is sequentially repeated, and the irradiation moves to the shallowest irradiation slice 901c.

Next, the function of the charged particle beam irradiation apparatus 1 according to this embodiment will be described.

The irradiation field preferably has a wide range in order to irradiate cancers in various body portions and with various sizes. Roughly speaking, there are two ways for broadening the irradiation field. First, series-connected two pairs of scanning electromagnets are located at a great distance from the patient to whom the charged particle beams are emitted. Second, the magnetic field strength of the outputs from the two pairs of scanning electromagnets is increased, or the axis length is elongated.

If the series-connected two pairs of scanning electromagnets are located at a great distance from the patient in order to secure a broad irradiation field, a great space is needed to install the charged particle beam irradiation apparatus. Therefore, a large housing may be needed for the apparatus. On the other hand, if the magnetic field strength of the outputs from the scanning electromagnets is increased, or the axis length is elongated, the magnetic field generation efficiency of the scanning electromagnets downstream in the beam movement direction is lowered. Therefore, the irradiation field may not be sufficiently obtained.

Under the circumstances, the inventors have used the pair of vertical scanning electromagnets 401a and the pair of horizontal scanning electromagnets 401b arranged in parallel to form the beam irradiation device 40. As a result, the elongation of the charged particle beam irradiation apparatus in the moving direction of the charged particle beam can be prevented, and an increase in aperture may be suppressed to a minimum level. Therefore, a charged particle beam irradiation apparatus that may suppress an increase in size and ensure a sufficient irradiation field may be provided.

Second Embodiment

A charged particle beam irradiation apparatus according to a second embodiment will be described with reference to FIG. 6. FIG. 6 is a diagram showing a scanning electromagnet 401A used in the charged particle beam irradiation apparatus according to the second embodiment. The charged particle beam irradiation apparatus according to the second embodiment has a structure obtained by replacing the scanning electromagnet 401 of the charged particle beam irradiation apparatus 1 according to the first embodiment shown in FIG. 1 with the scanning electromagnet 401A shown in FIG. 6.

The scanning electromagnet 401A has a structure in which three scanning electromagnets 401 shown in FIG. 2 are arranged in series along the moving direction of the charged particle beam 104c. Specifically, the scanning electromagnet 401A includes a pair of vertical scanning electromagnets $401a_1$ and a pair of horizontal scanning electromagnets $401b_1$ that are disposed in parallel with the moving direction of the charged particle beam 104c, a pair of vertical scanning electromagnets $401a_2$ and a pair of horizontal scanning electromagnets $401b_2$ that are disposed after the scanning electromagnets $401a_1$ and $401b_1$ in parallel with the moving direction of the charged particle beam 104c, and a pair of vertical scanning electromagnets $401a_3$ and a pair of horizontal scanning electromagnets $401b_3$ that are disposed after the scanning electromagnets $401a_2$ and $401b_2$ in parallel with the moving direction of the charged particle beam 104c.

The aperture of the scanning electromagnet increases from the inlet side to the outlet side. Specifically, the aperture formed by the pair of vertical scanning electromagnets $401a_2$ and the pair of horizontal scanning electromagnets $401b_2$ is greater than the aperture formed by the pair of vertical scanning electromagnets $401a_1$ and the pair of horizontal scanning electromagnets $401b_1$, and the aperture formed by the pair of vertical scanning electromagnets $401a_3$ and the pair of horizontal scanning electromagnets $401b_3$ is greater than the aperture formed by the pair of vertical scanning electromagnets $401a_2$ and the pair of horizontal scanning electromagnets $401b_2$.

The structure in which two or more scanning electromagnets shown in FIG. 2 are arranged in series, and the aperture increases from the scanning electromagnet on the inlet side to the scanning electromagnet on the outlet side prevents the charged particle beam irradiation apparatus from elongating in the moving direction of the charged particle beam, and suppresses an increase in the aperture to a minimum level, like the structure of the first embodiment. Therefore, a charged particle beam irradiation apparatus that may suppress an increase in size, and ensure a sufficient irradiation field may be provided.

Third Embodiment

Figure 7:
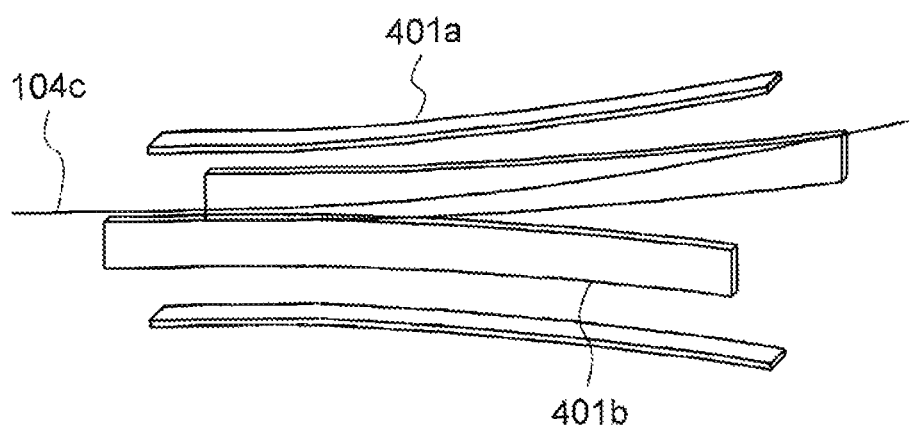
FIG. 7 is a diagram showing scanning electromagnets included in a charged particle beam irradiation apparatus according to a third embodiment.

A charged particle beam irradiation apparatus according to a third embodiment will be described with reference to FIG. 7. FIG. 7 is a diagram showing a scanning electromagnet 401B of the charged particle beam irradiation apparatus according to the third embodiment. The charged particle beam irradiation apparatus according to the third embodiment has a structure in which the scanning electromagnet 401 of the charged particle beam irradiation apparatus 1 according to the first embodiment shown in FIG. 1 is replaced by the scanning electromagnet 401B shown in FIG. 7.

The scanning electromagnet 401B includes a pair of vertical scanning electromagnets 401a and a pair of horizontal scanning electromagnets 401b arranged in parallel. The pair of vertical scanning electromagnets 401a and the pair of horizontal scanning electromagnets 401b have an aperture that increases from the charged particle beam 104c inlet side to the charged particle beam 104c outlet side. Although the shape of the increasing aperture is like a trumpet that matches the deflection of the beam in FIG. 7, the aperture may linearly increase from the charged particle beam 104c inlet side to the charged particle beam 104c outlet side.

Figure 8:
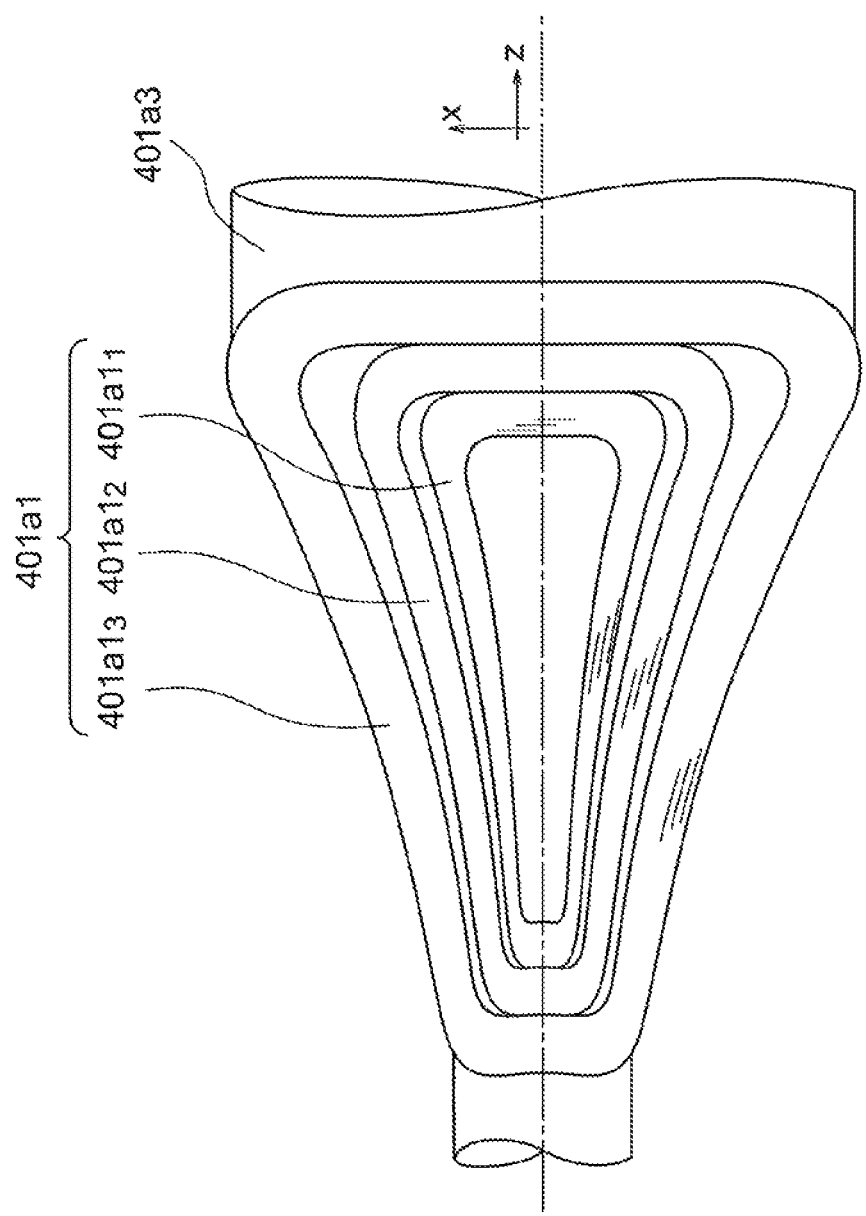
FIG. 8 is an explanatory diagram of a vertical scanning electromagnet according to the third embodiment.

FIG. 8 shows an upper coil device 401a1 of the vertical scanning electromagnets 401a in the third embodiment. The vertical scanning electromagnets 401a have a hollow structure 401a3, the aperture of which increases from the charged particle beam 104c inlet side to the charged particle beam 104c outlet side. The upper coil device $401a1_1$ is disposed on the upper surface of the structure 403a3.

The upper coil device $401a1_1$ includes a coil $401a1_1$ disposed on the upper surface of the structure 403a3, a coil $401a1_2$ disposed outside the coil $401a1_1$, and a coil $401a1_3$ disposed outside the coil $401a1_2$.

As in the case shown in FIGS. 3A to 3C, the vertical scanning electromagnets 401a include a lower coil device (not shown) disposed on the lower surface of the structure 401a3. Like the upper coil device 401a1, the lower coil device includes a plurality of coils, which are disposed on the lower surface of the structure. Although three coils each are disposed on the upper side and the lower side in FIG. 8, the number of coils may be one, two, or four or more.

Like the case shown in FIGS. 4A to 4C, coil devices of the horizontal scanning electromagnets are disposed outside or inside the vertical scanning electromagnets 401a.

Like the structure of the first embodiment, the above structure of the third embodiment is capable of preventing the charged particle beam irradiation apparatus from elongating along the moving direction of the charged particle beam, and suppressing an increase in the aperture to a minimum level. Therefore, a charged particle beam irradiation apparatus that may suppress an increase in size, and ensure a sufficient irradiation field may be provided.

Fourth Embodiment

A charged particle beam irradiation apparatus according to a fourth embodiment will be described with reference to FIG. 9. FIG. 9 is a diagram showing a scanning electromagnet 401C included in the charged particle beam irradiation apparatus according to the fourth embodiment. The charged particle beam irradiation apparatus according to the fourth embodiment has a structure obtained by replacing the scanning electromagnet 401 of the charged particle beam irradiation apparatus 1 according to the first embodiment shown in FIG. 1 with a scanning electromagnet 401C shown in FIG. 9.

The scanning electromagnet 401C includes a first scanning electromagnet device $401C_1$, and a second scanning electromagnet device $401C_2$ disposed after the first scanning electromagnet device $401C_1$. The first scanning electromagnet device $401C_1$ includes a pair of vertical scanning electromagnets $410a_1$ and a pair of horizontal scanning electromagnets $410b_1$ arranged in parallel with a charged particle beam 104c that enters the first scanning electromagnet device $401C_1$, and has a structure with the aperture being substantially constant or linearly increasing from the inlet side to the outlet side. Thus, the first scanning electromagnet device $401C_1$ has a structure in which the rate of change in aperture from the inlet side to the outlet side is substantially zero or a constant positive value. The rate of change in aperture means the ratio $\Delta D/\Delta z$ when the aperture increases $\Delta D$ for the distance $\Delta z$ from the inlet side to the outlet side.

The second scanning electromagnet device $401C_2$ includes a pair of vertical scanning electromagnets $410a_2$ and a pair of horizontal scanning electromagnets $410b_2$ arranged in parallel with one another, and is configured such that the aperture linearly increases from the inlet side to the outlet side with a rate of change that is different from the rate of change for the first scanning electromagnet device $401C_1$. The aperture on the outlet side of the first scanning electromagnet device $401C_1$ is substantially equal to the aperture on the inlet side of the second scanning electromagnet device $401_2$.

Figure 10:
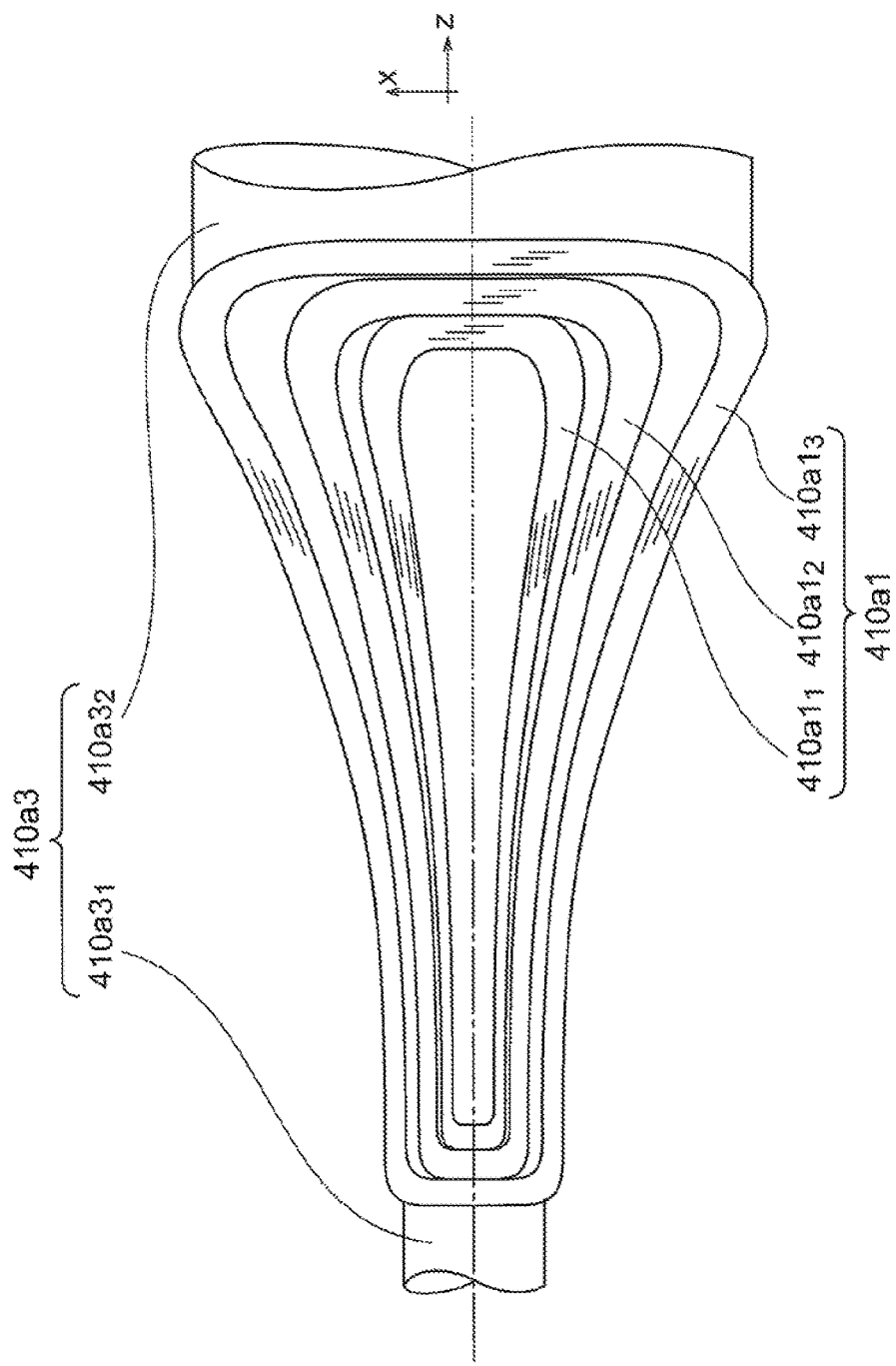
FIG. 10 is an explanatory diagram of a vertical scanning electromagnet according to the fourth embodiment.

FIG. 10 shows a specific example of a structure 410a3 relating to the vertical scanning electromagnets $410a_1$ and the vertical scanning electromagnets $410a_2$ according to the fourth embodiment, and a first coil device 410a1 disposed on the upper surface of the structure 410a3. The structure 410a3 includes a first portion $410a3_1$ and a second portion $410a3_2$ connecting to the first portion $410a3_1$. The first coil device 410a1 includes coils that integrally make the vertical scanning electromagnet $410a_1$ and the vertical scanning electromagnet $410a2$.

The first coil device 410a1 includes a coil $410a1_1$ disposed on the upper surface of the structure 410a3, a coil $410a1_2$ disposed outside the coil $410a1_1$, and a coil $410a1_3$ disposed outside the coil $410a1_2$. Like the first embodiment, the coils $410a1_1$, $410a1_2$, and $410a1_3$ are coated with an insulating material. A vertical magnetic field is generated by causing an excitation current to flow through the coils $410a1_1$, $410a1_2$, and $410a1_3$ by means of the electromagnet power supply 402a shown in FIG. 1. Although three coils are disposed on the upper surface of the structure in FIG. 10, the number of coils may be one, two, or four or more.

The first portion $410a3_1$ is hollow, like the structure 401a3 of the first embodiment shown in FIGS. 3A, 3B, and 3C. The second portion $410a3_2$ has a tube-like shape with the aperture linearly increasing from the inlet side to the outlet side. The aperture on the outlet side of the first portion $410a3_1$ is substantially equal to the aperture on the inlet side of the second portion $410a3_2$. The coils $410a1_1$, $410a1_2$, and $410a1_3$ are shaped to cover the first portion $410a3_1$ and the second portion $410a3_2$.

The second coil device (not shown) of the pair of vertical scanning electromagnets $410a_1$ and the pair of vertical scanning electromagnets $410a_2$ is disposed on the lower surface of the first part $410a3_1$ and the second part $410a3_2$, like the first embodiment shown in FIGS. 3A, 3B, and 3C. The second coil device also includes three coils, like the first coil device $410a1_1$ shown in FIG. 10. As in the first embodiment shown in FIGS. 3A, 3B, and 3C, the respective coils of the second coil device have the same sizes as the coils $410a1_1$, $410a1_2$, and $410a1_3$ of the first coil device $410a1$, and are arranged to be symmetrical to the coils $410a1_1$, $410a1_2$, and $410a1_3$ of the first coil device $410a1$ relative to the central axis of the first portion $410a3_1$ and the second portion $410a3_2$.

Figure 11:
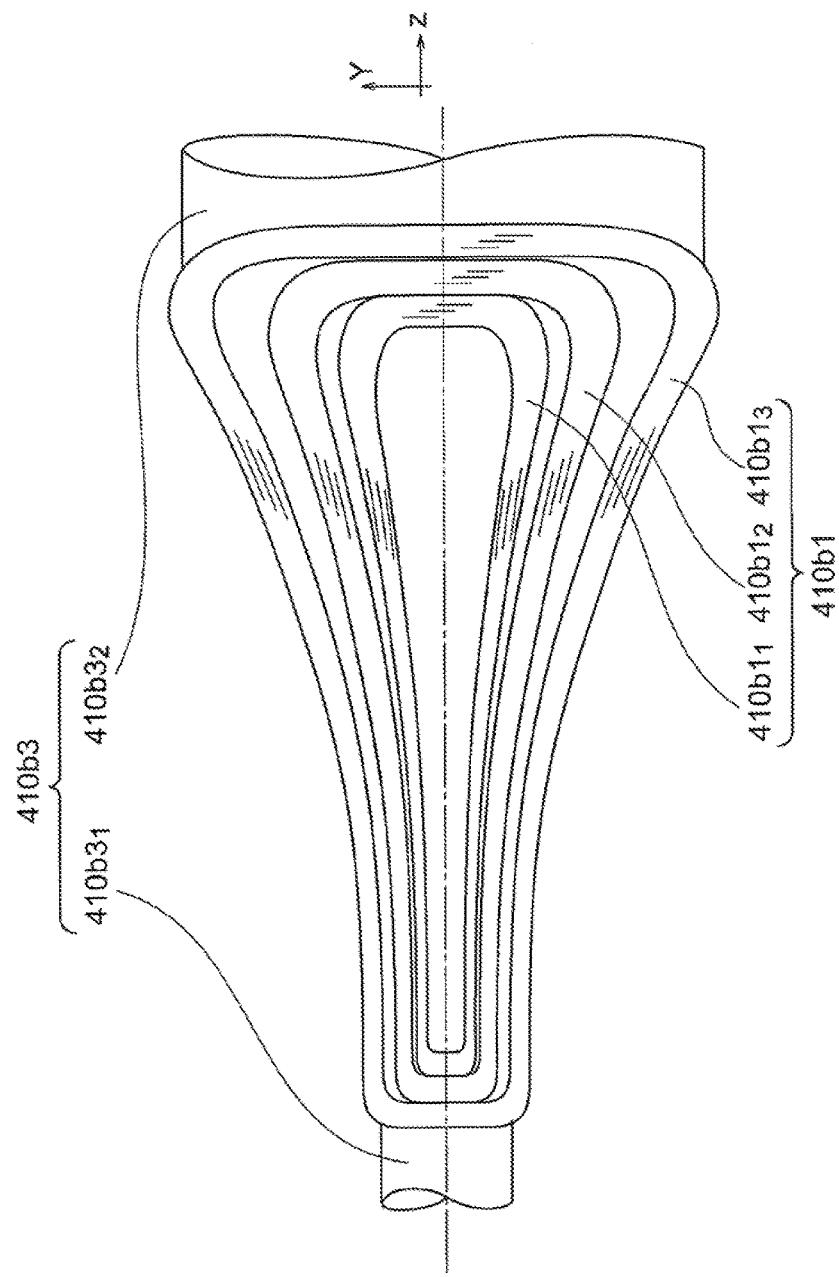
FIG. 11 is an explanatory diagram of a horizontal scanning electromagnet according to the fourth embodiment.

The horizontal scanning electromagnets $410a_1$ and the horizontal scanning electromagnets $410b_2$ of the fourth embodiment include a structure $410b3$, a first coil device $410b1$ disposed on one of the side surfaces of the structure $410b3$, and a second coil device (not shown) disposed on the other of the side surface, as shown in FIG. 11.

The structure $410b3$ is disposed outside the vertical scanning electromagnets $410a_1$ and the vertical scanning electromagnets $410a2$, and includes a first portion $410b1_1$ and a second portion $410b1_2$ connecting to the first portion $410b1_1$. The first portion $410a3_1$ is hollow, like the structure $401a3$ of the first embodiment shown in FIGS. 3A, 3B, and 3C. The second portion $410a3_2$ has a tube-like shape with the aperture linearly increasing from the inlet side to the outlet side. The aperture on the outlet side of the first portion $410a3_1$ is substantially equal to the aperture on the inlet side of the second portion $410a3_2$. The horizontal scanning electromagnets $410b_1$ and $410b_2$ may be disposed inside the vertical scanning electromagnets $410a_1$ and $410a_2$.

The first coil device $410b1$ includes a coil $410b1_1$ disposed on one of the side surfaces of the structure $410b3$, a coil $410b1_2$ disposed outside the coil $410b1_1$, and a coil $410b1_3$ disposed outside the coil $410b1_2$. The coils $410b1_1$, $410b1_2$, and $410b1_3$ are shaped to cover the first portion $410b3_1$ and the second portion $410b3_2$. As in the first embodiment, the coils $410b1_1$, $410b1_2$, and $410b1_3$ are coated with an insulating material. A horizontal magnetic field is generated by causing an excitation current to flow through the coils $410b1_1$, $410b1_2$, and $410b1_3$ by means of the electromagnet power supply $402b$ shown in FIG. 1. Although three coils are disposed on the one of the side surfaces of the structure in FIG. 11, the number of coils may be one, two, or four or more.

The second coil device (not shown) of the pair of horizontal scanning electromagnets $410b_1$ and the pair of horizontal scanning electromagnets $410b_2$ is disposed on the other of the side surfaces of the first portion $410b3_1$ and the second portion $410b3_2$, as in the first embodiment shown in FIGS. 4A, 4B, and 4C. Like the first coil device $410b1$ shown in FIG. 11, the second coil device includes three coils. As in the first embodiment shown in FIGS. 4A, 4B, and 4C, the respective coils of the second coil device have substantially the same sizes as the coils $410b1_1$, $410b1_2$, and $410b1_3$ of the first coil device $410b1$, and are arranged to be symmetrical to the coils $410b1_1$, $410b1_2$, and $410b1_3$ of the first coil device $410b1$ relative to the central axis of the first portion $410b3_1$ and the second portion $410b3_2$.

In the fourth embodiment shown in FIG. 9, the scanning electromagnet $401C$ includes the pair of vertical scanning electromagnets $410a_1$ and the pair of horizontal scanning electromagnets $410b_1$ arranged to be parallel with the charged particle beam $104c$, and the pair of vertical scanning electromagnets $410a_2$ and the pair of horizontal scanning electromagnets $410b_2$ arranged in parallel after the scanning electromagnets $410a_1$ and $410b_1$. The aperture of the scanning electromagnets $410a_2$ and $410b_2$ linearly increases from the inlet side to the outlet side. Accordingly, like the first embodiment, the charged particle beam irradiation apparatus is prevented from elongating along the moving direction of the charged particle beam, and the aperture is suppressed to a minimum level. Therefore, a charged particle beam irradiation apparatus that suppresses an increase in size, and ensures a sufficient irradiation field may be provided.

Although the fourth embodiment has a two-stage structure in which the scanning electromagnet $401C$ has the first scanning electromagnet device $401C_1$ and the second scanning electromagnet device $401C_2$ arranged after the first scanning electromagnet device $401C_1$, it may have three or more stages. For example, the fourth embodiment may have a three-stage structure in which the scanning electromagnet $401C$ has a first scanning electromagnet device $401C_1$, a second scanning electromagnet device $401C_2$ arranged after the first scanning electromagnet device $401C_1$, and a third scanning electromagnet arranged after the second scanning electromagnet device $401C_2$, and the aperture of the third scanning electromagnet may linearly increase from the inlet side to the outlet side with a rate of change that is different from the rate of change of the second scanning electromagnet device $401C_2$. Such a three-stage structure may also be applied to fifth to eighth embodiments that will be described later.

Fifth Embodiment

A charged particle beam irradiation apparatus according to a fifth embodiment will be described with reference to FIGS. 12 and 13. The charged particle beam irradiation apparatus 1 according to the fifth embodiment has a structure in which each of the vertical scanning electromagnets $410a_1$ and $410a_2$ shown in FIG. 9 includes corresponding coils, and each of the horizontal scanning electromagnets $410b_1$ and $410b_2$ includes corresponding coils.

Figure 12:
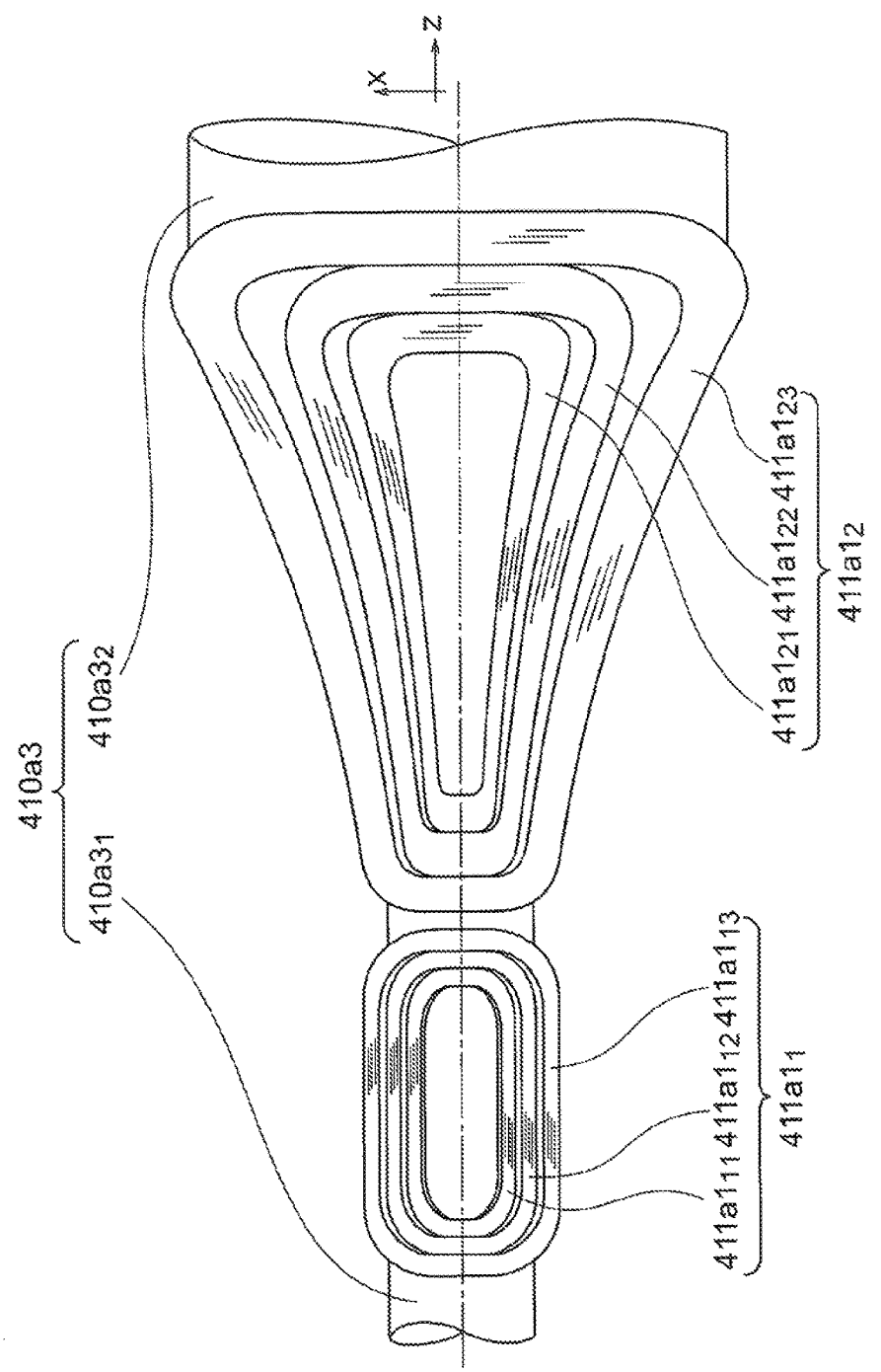
FIG. 12 is an explanatory diagram of vertical scanning electromagnets according to a fifth embodiment.

FIG. 12 is a diagram showing first coil devices $411a1_1$ and $411a1_2$ disposed on the upper surface of the structure $410a3$ at portions corresponding to the vertical scanning electromagnets $410a_1$ and $410a_2$ in the fifth embodiment. The first coil device $411a1_1$ is disposed on the upper surface of the first portion $410a3_1$ and includes a coil $411a1_{11}$, a coil $411a1_{12}$ disposed outside the coil $411a1_1$, and coil $411a1_{13}$ disposed outside the coil $411a1_{12}$. The second coil device $411a1_2$ is disposed on the upper surface of the second portion $410a3_2$, and includes a coil $411a1_{21}$, a coil $411a1_{22}$ disposed outside the coil $411a1_{21}$, and a coil $411a1_{23}$ disposed outside the coil $411a1_{22}$. Thus, the first coil devices $411a1_1$ and $411a1_2$ of the fifth embodiment have a structure obtained by dividing the first coil device $410a1$ shown in FIG. 10 into two. Although three coils each are disposed on the first coil devices on the upper surface of the structure in FIG. 12, the number of coils may be one, two, or four or more.

The second coil devices (not shown) that make pairs with the first coil devices $411a1_1$ and $411a1_2$ are disposed on the lower surfaces of the first portion $410a3_1$ and the second portion $410a3_2$, as in the first embodiment shown in FIGS. 3A, 3B, and 3C. Like the first coil devices $411a1_1$ and $411a1_2$ shown in FIG. 12, the second coil devices each include three coils. As in the first embodiment shown in FIGS. 3A, 3B, and 3C, the respective coils of the second coil device disposed on the lower surface of the first portion $410a3_1$ have the same sizes as the coils $411a1_{11}$, $411a1_{12}$, and $411a1_{13}$ of the first coil device $411a1_1$, and are arranged to be symmetrical to the coils $411a1_{11}$, $4a1_{12}$, and $411a1_{13}$ of the first coil device $411a1_1$ relative to the central axis of the first portion $410a3_1$. The respective coils of the second coil device disposed on the lower surface of the second portion $410a3_2$ have the same sizes as the coils $411a1_{21}$, $411a1_{22}$, and $411a1_{23}$ of the first coil device $411a1_2$, and are arranged to be symmetrical to the coils $411a1_{21}$, $411a1_{22}$, and $411a1_{23}$ of the first coil device $411a_2$ relative to the central axis of the second portion $410a3_2$.

Figure 13:
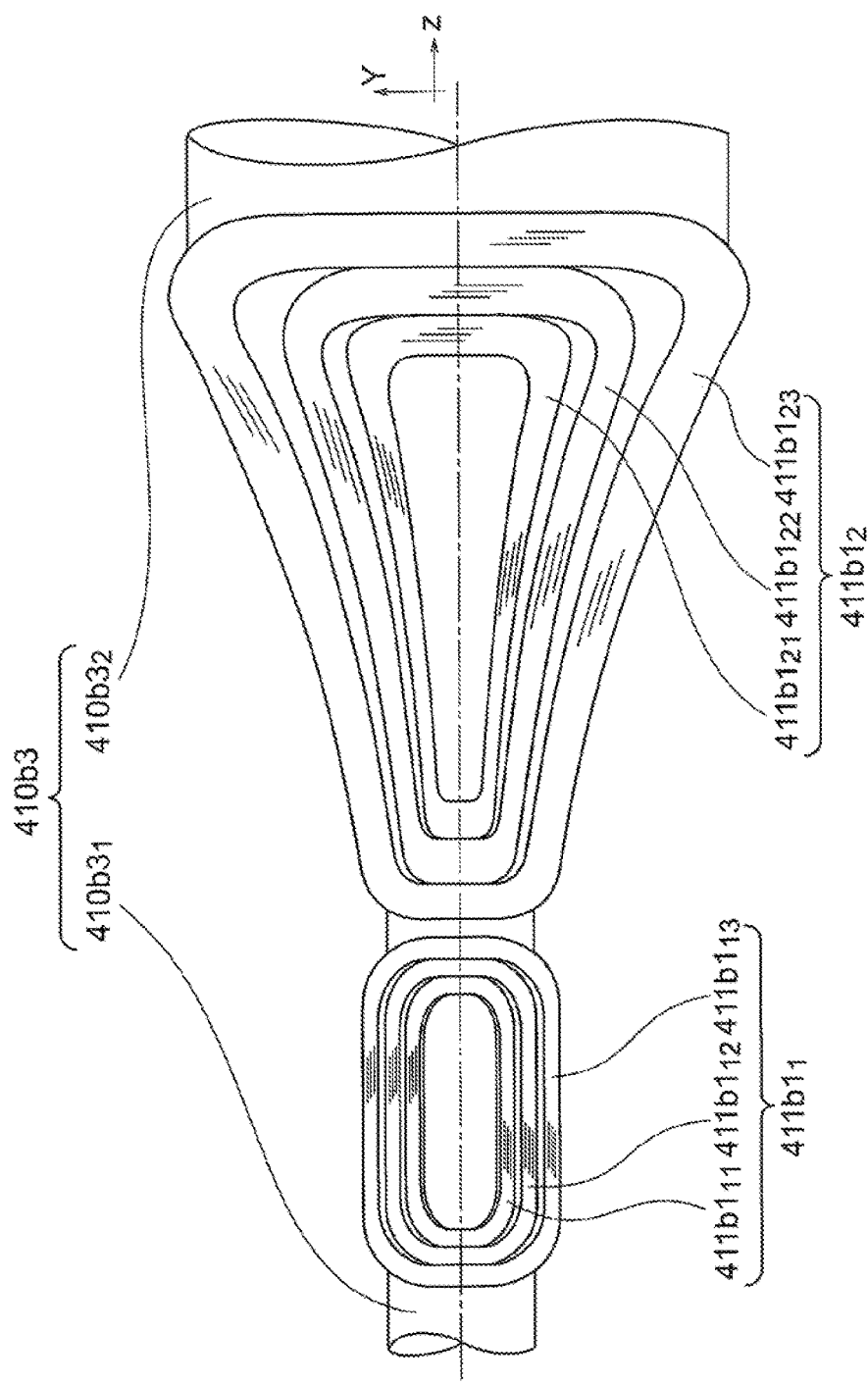
FIG. 13 is an explanatory diagram of horizontal scanning electromagnets according to the fifth embodiment.

FIG. 13 is a diagram showing first coil devices $411b1_1$ and $411b1_2$ disposed on one of the side surfaces of the structure $410b3$ at portions corresponding to the horizontal scanning electromagnets $410b_1$ and $410b_2$ in the fifth embodiment. The first coil device $411b1_1$ is disposed on one of the side surfaces of the first portion $410b3_1$, and includes a coil $411b1_1$, a coil $411b1_{12}$ disposed outside the coil $411b1_{11}$, and a coil $411b1_{13}$ disposed outside the coil $411b1_{12}$. The first coil device $411b1_2$ is disposed on one of the side surfaces of the second portion $410b_2$, and includes a coil $411b1_{21}$, a coil $411b1_{22}$ disposed outside the coil $411b1_{21}$, and a coil $411b1_{23}$ disposed outside the coil $411b1_{22}$. Thus, the first coil devices $411b1_1$ and $411b1_2$ of the fifth embodiment have a structure obtained by dividing the first coil device $410b1$ shown in FIG. 11 into two. Although three coils each are disposed on the one of the side surfaces of the structure in FIG. 13, the number of coils may be one, two, or four or more.

The second coil devices (not shown) that make pairs with the first coil devices $411b1_1$ and $411b1_2$ are disposed on the other of the side surfaces of the first portion $410b3_1$ and the second portion $410b3_2$, as in the first embodiment shown in FIGS. 4A, 4B, and 4C. Like the first coil devices $411b1_1$ and $411b1_2$ shown in FIG. 13, the second coil devices each include three coils. As in the first embodiment shown in FIGS. 4A, 4B, and 4C, the respective coils of the second coil device disposed on the other of the side surface the first portion $410b3_1$ have the same sizes as the coils $411b1_{11}$, $411b1_{12}$, and $411b1_{13}$ of the first coil device $411b1_1$, and are arranged to be symmetrical to the coils $411b1_{11}$, $411b1_{12}$, and $411b1_{13}$ of the first coil device $411b1_1$ relative to the central axis of the first portion $410b3_1$. The respective coils of the second coil device disposed on the other of the side surfaces of the second portion $410b3_2$ have the same sizes as the coils $411b1_{21}$, $411b1_{22}$, and $411b1_{23}$ of the first coil device $411b1_2$ and are arranged to be symmetrical to the coils $411b1_{21}$, $411b1_{22}$, and $411b1_{23}$ of the first coil device $411b_2$ relative to the central axis of the second portion $410b3_2$.

In the fifth embodiment having the above structure, the intensity of the excitation current flowing through the pair of vertical scanning electromagnets $410a_1$ may be different from the intensity of the excitation current flowing through the pair of vertical scanning electromagnets $410a_2$, and the intensity of the excitation current flowing through the pair of horizontal scanning electromagnets $410b_1$ may be different from the intensity of the excitation current flowing through the pair of horizontal scanning electromagnets $410b_2$. Therefore, the intensity of the magnetic field generated by the pair of vertical scanning electromagnets $410a_2$ and the pair of horizontal scanning electromagnets $410b_2$ having the aperture linearly increasing from the inlet side to the outlet side may be adjusted more easily than that of the fourth embodiment. In this case, a first electromagnet power supply that supplies an excitation current to the pair of vertical scanning electromagnets $410a_1$ and a second electromagnet power supply that supplies an excitation current to the pair of vertical scanning electromagnets $410a_2$ are preferably prepared. Furthermore, a third electromagnet power supply that supplies an excitation current to the pair of horizontal scanning electromagnets $410b_1$ and a fourth electromagnet power supply that supplies an excitation current to the pair of horizontal scanning electromagnets $410b_2$ are preferably prepared.

Like the structure of the fourth embodiment, the above structure of the fifth embodiment is capable of preventing the charged particle beam irradiation apparatus from elongating along the moving direction of the charged particle beam, and suppressing an increase in the aperture to a minimum level. Therefore, a charged particle beam irradiation apparatus that suppresses an increase in size, and ensures a sufficient irradiation field may be provided.

Sixth Embodiment

A charged particle beam irradiation apparatus according to a sixth embodiment will be described with reference to FIGS. 14 and 15. The charged particle beam irradiation apparatus according to the sixth embodiment has a structure in which the number of coils included in the pair of vertical scanning electromagnets $410a_2$ and the pair of horizontal scanning electromagnets $410b_2$ is greater than the number coils included in the pair of vertical scanning electromagnets $410a_1$ and the pair of horizontal scanning electromagnets $410b_1$ in the charged particle beam irradiation apparatus 1 according to the fifth embodiment.

Figure 14:
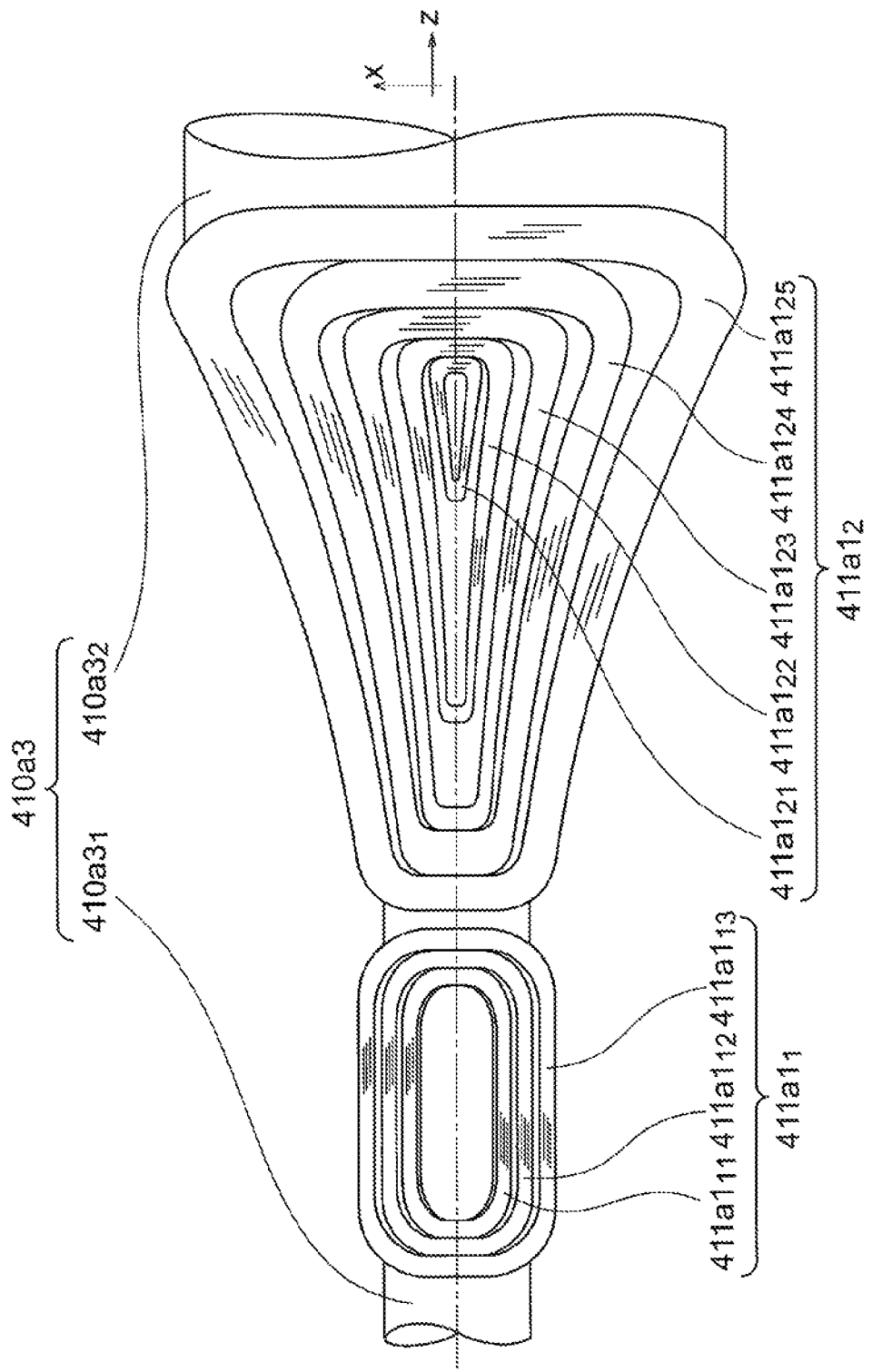
FIG. 14 is an explanatory diagram of vertical scanning electromagnets according to a sixth embodiment.

FIG. 14 is a diagram showing first coil devices $411a1_1$ and $411a1_2$ disposed on the upper surface of a structure $410a3$ at portions corresponding to the vertical scanning electromagnets $410a_1$ and $410a_2$ in the sixth embodiment. The first coil device $411a1_1$ is disposed on the upper surface of the first portion $410a3_1$, and includes a coil $411a1_{11}$, a coil $411a1_{12}$ disposed outside the coil $411a1_{11}$, and a coil $411a1_{13}$ disposed outside the coil $411a1_2$. The first coil device $411a1_2$ is disposed on the upper surface of the second portion $410a3_2$, and includes a coil $411a1_{21}$, a coil $411a1_{22}$ disposed outside the coil $411a1_{21}$, a coil $411a1_{23}$ disposed outside the coil $411a1_{22}$, a coil $411a1_{24}$ disposed outside the coil $411a1_{23}$, and a coil $411a1_{25}$ disposed outside the coil $411a1_{24}$. Although the first coil device $411a1$ has three coils on the upper surface of the first portion $410a3_1$ in FIG. 14, the number of coils may be one, two, or four or more. Although the first coil device $411a1_2$ has five coils on the upper surface of the second portion $410a3_2$, any number of coils may be disposed if the number is greater than the number of coils of the first coil device $411a1_1$.

The second coil devices (not shown) that make pairs with the first coil devices $411a1_1$ and $411a1_2$ are disposed on the lower surfaces of the first portion $410a3_1$ and the second portion $410a3_2$, as in the first embodiment shown in FIGS. 3A, 3B, and 3C. Like the first coil device $411a1_1$ and the first coil device $411a1_2$ shown in FIG. 14, the second coil devices include three coils and five coils, respectively. As in the first embodiment shown in FIGS. 3A, 3B, and 3C, the respective coils of the second coil devices disposed on the lower surface of the first portion $410a3_1$ have the same sizes as the coils $411a1_{11}$, $411a1_{12}$, and $411a1_{13}$ of the first coil device $411a1_1$, and are arranged to be symmetrical to the coils $411a1_{11}$, $411a1_{12}$, and $411a1_{13}$ of the first coil device $411a1_1$ relative to the central axis of the first portion $410a3_1$. The respective coils of the second coil device disposed on the lower surface of the second portion $410a3_2$ have the same sizes as the coils $411a1_{21}$, $411a1_{22}$, $411a1_{23}$, $411a1_{24}$, and $411a1_{25}$ of the first coil device $411a1_2$, and are arranged to be symmetrical to the coils $411a1_{21}$, $411a1_{22}$, $411a1_{23}$, $411a1_{24}$, and $411a1_{25}$ of the first coil device $411a2$ relative to the central axis of the second portion $410a3_2$.

Figure 15:
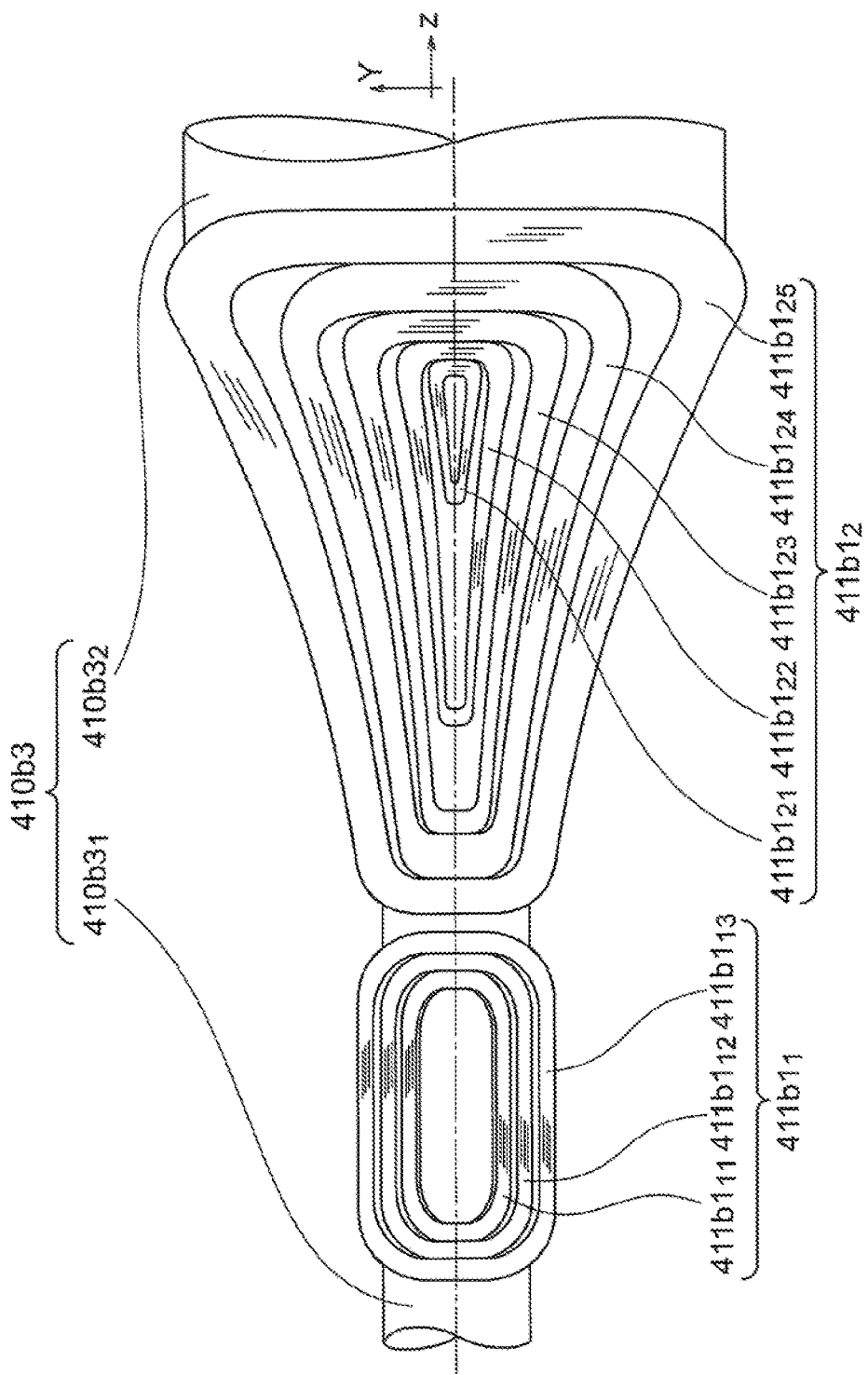
FIG. 15 is an explanatory diagram of horizontal scanning electromagnets according to the sixth embodiment.

FIG. 15 is a diagram showing the first coil devices $411b1_1$ and $411b1_2$ disposed on one of the side surfaces of the structure $410b3$ at portions corresponding to the horizontal scanning electromagnets $410b_1$ and $410b_2$ in the sixth embodiment. The first coil device $411b1_1$ is disposed on one of the side surfaces of the first portion $410b3_1$, and includes a coil $411b1_{11}$, a coil $411b1_{12}$ disposed outside the coil $411b1_{11}$, and a coil $411b1_{13}$ disposed outside the coil $411b1_{12}$. The first coil device $411b1_2$ is disposed on one of the side surfaces of the second portion $410b3_2$, and includes a coil $411b1_{21}$, a coil $411b1_{22}$ disposed outside the coil $411b1_{21}$, a coil $411b1_{23}$ disposed outside the coil $411b1_{22}$, a coil $411b1_{24}$ disposed outside the coil $411b1_{23}$, and a coil $411b1_{25}$ disposed outside the coil $411b1_{24}$. Although the first coil device $411b1_1$ has three coils on the one of the side surfaces of the first portion $410b3_1$ in FIG. 15, the number of coils may be one, two, or four or more. Although the first coil device $411b1_2$ has five coils on the one of the side surfaces of the second portion $410b3_2$, any number of coils may be disposed if the number is greater than the number of coils of the first coil device $411b1_1$.

The second coil devices (not shown) that make pairs with the first coil devices $411b1_1$ and $411b1_2$ are disposed on the other of the surfaces of the first portion $410b3_1$ and the second portion $410b3_2$, as in the first embodiment shown in FIGS. 4A, 4B, and 4C. Like the first coil device $411b1_1$ and the first coil device $411b1_2$ shown in FIG. 15, the second coil devices include three coils and five coils, respectively. As in the first embodiment shown in FIGS. 3A, 3B, and 3C, the respective coils of the second coil device disposed on the other of the side surfaces or the first portion $410a3_1$ have the same sizes as the coils $411b1_{11}$, $411b1_{12}$, and $411b1_{13}$ of the first coil device $411b1_1$, and are arranged to be symmetrical to the coils $411b1_{11}$, $411b1_{12}$, and $411b1_{13}$ of the first coil device $411b1_1$ relative to the central axis of the first portion $410b3_1$. The respective coils of the second coil device disposed on the other of the side surfaces of the second portion $410b3_2$ have the same sizes as the coils $411b1_{21}$, $411b1_{22}$, $411b1_{23}$, $411b1_{24}$, and $411b1_{25}$ of the first coil device $411b1_2$, and are arranged to be symmetrical to the coils $411b1_{21}$, $411b1_{22}$, $411b1_{23}$, $411b1_{24}$, and $411b1_{25}$ of the first coil device $411b_2$ relative to the central axis of the second portion $410b3_2$.

In the sixth embodiment having the above structure, the intensity of the magnetic field generated by the pair of vertical scanning electromagnets $410a_2$ is greater than the intensity of the magnetic field generated by the pair of vertical scanning electromagnets $410a_1$ if the excitation current having the same value is caused to flow through the pair of vertical scanning electromagnets $410a_1$ and the pair of vertical scanning electromagnets $410a_2$ since the number of coils differs between the pair of vertical scanning electromagnets $410a_1$ and the pair of vertical scanning electromagnets $410a_2$. Therefore, the excitation current may be supplied to the pair of vertical scanning electromagnets $410a_1$ and the pair of vertical scanning electromagnets $410a_2$ by means of the same electromagnet power supply.

Furthermore, since the number of coils differs between the pair of horizontal scanning electromagnets $410b_1$ and the pair of horizontal scanning electromagnets $410b_2$, the intensity of the magnetic field generated by the pair of horizontal scanning electromagnets $410b_2$ is greater than the intensity of the magnetic field generated by the pair of horizontal scanning electromagnets $410b_1$ if the same value of excitation current is caused to flow through the pair of horizontal scanning electromagnets $410b_1$ and the pair of horizontal scanning electromagnets $410b_2$. Therefore, the same electromagnet power supply may be used to supply an excitation current to the pair of horizontal scanning electromagnets $410b_1$ and the pair of horizontal scanning electromagnets $410b_2$.

Like the structure of the fifth embodiment, the above structure of the sixth embodiment is capable of preventing the charged particle beam irradiation apparatus from elongating along the moving direction of the charged particle beam, and suppressing an increase in the aperture to a minimum level. Therefore, a charged particle beam irradiation apparatus that suppresses an increase in size, and ensures a sufficient irradiation field may be provided.

Seventh Embodiment

A charged particle beam irradiation apparatus according to a seventh embodiment will be described with reference to FIGS. 16 and 17. The charged particle beam irradiation apparatus according to the seventh embodiment has a structure in which the number of coils included in the pair of vertical scanning electromagnets $410a_2$ and the pair of horizontal scanning electromagnets $410b_2$ is greater than the number of coils included in the pair of vertical scanning electromagnets $410a_1$ and the pair of horizontal scanning electromagnets $410b_1$ in the charged particle beam irradiation apparatus 1 according to the fourth embodiment.

Figure 16:
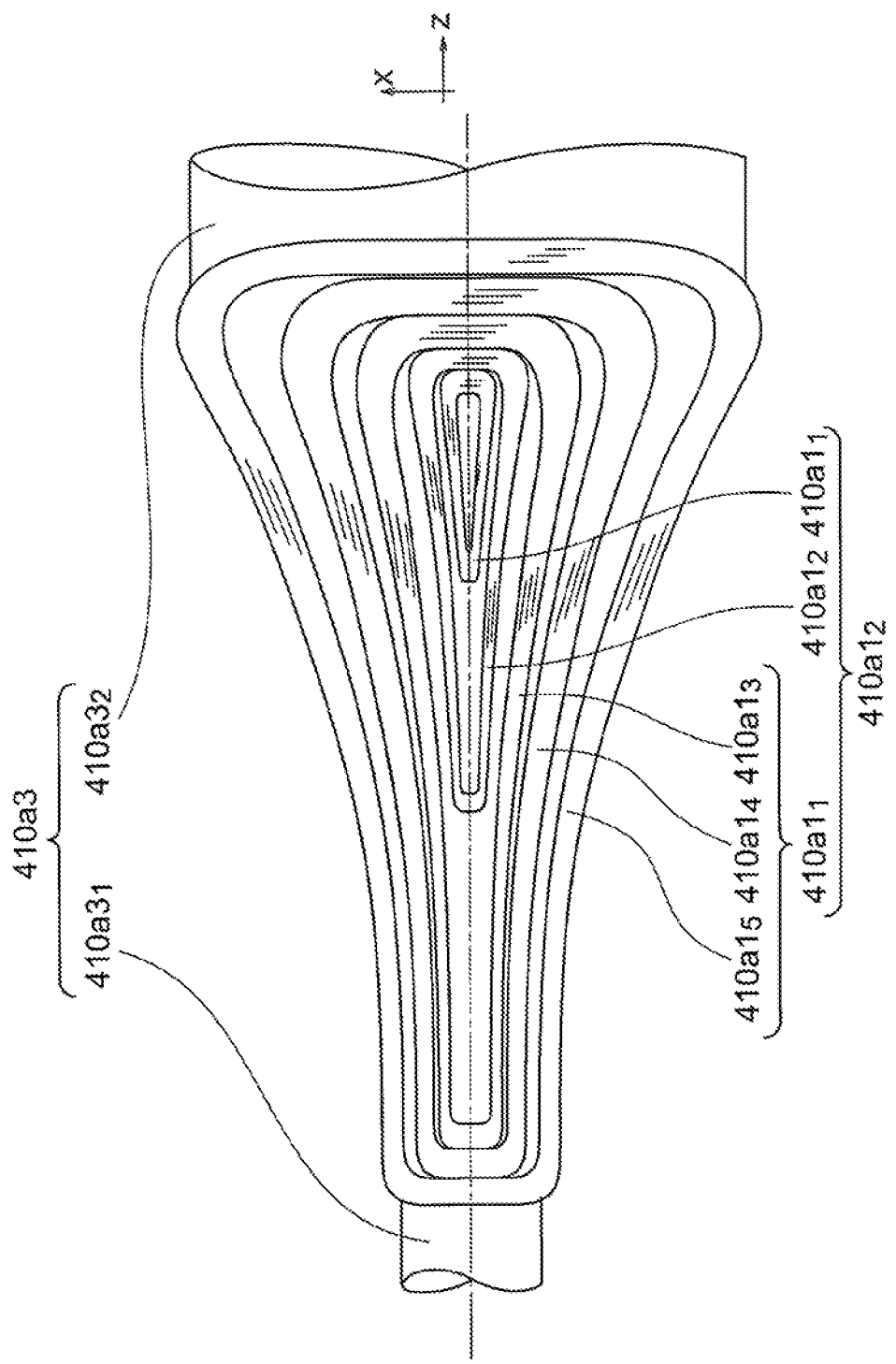
FIG. 16 is an explanatory diagram of a vertical scanning electromagnet according to a seventh embodiment.

FIG. 16 is a diagram showing first coil devices $410a1_1$ and $410a1_2$ disposed on the upper surface of a structure $410a3$ at portions corresponding to vertical scanning electromagnets $410a_1$ and $410a_2$ in the seventh embodiment. The first coil device $410a1_2$ is disposed on the upper surface of the second portion $410a3_2$, and includes a coil $410a1_1$, a coil $410a1_2$ disposed outside the coil $410a1_1$, a coil $410a1_3$ disposed outside the coil $410a1_2$, a coil $410a1_4$ disposed outside the coil $410a1_3$, and a coil $410a1_5$ disposed outside the coil $410a1_4$. The coil $410a1_3$, the coil $410a1_4$, and the coil $410a1_5$ extend over the upper surface of the first portion $410a3_1$ to form the first coil device $410a1_1$. Although the first coil device $410a1_1$ has three coils in FIG. 16, the number of coils may be one, two, or four or more. Although the first coil device $410a1_2$ has five coils, any number of coils may be disposed if the number is greater than the number of coils of the first coil device $410a1_1$.

The second coil devices (not shown) that make pairs with the first coil devices $410a_1$ and $410a1_2$ are disposed on the lower surfaces of the first portion $410a3_1$ and the second part $410a3_2$, as in the first embodiment shown in FIGS. 3A, 3B, and 3C. Like the first coil device $410a1_1$ and the first coil device $410a1_2$ shown in FIG. 16, the second coil devices include three coils and five coils, respectively. As in the first embodiment shown in FIGS. 3A, 3B, and 3C, the respective coils of the second coil device disposed on the lower surface of the first portion $410a3_1$ have the same sizes as the coils $410a1_3$, $410a1_4$, and $410a1_5$ of the first coil device $410a1_1$, and are arranged to be symmetrical to the coils $410a1_3$, $410a1_4$, and $410a1_5$ of the first coil device $410a1_8$ relative to the central axis of the first portion $410a3_1$. The respective coils of the second coil device disposed on the lower surface of the second portion $410a3_2$ have the same sizes as the coils $410a1_1$, $410a1_2$, $410a1_3$, $410a1_4$, and $410a1_5$ of the first coil device $410a1_2$, and are arranged to be symmetrical to the coils $410a1_1$, $410a1_2$, $410a1_3$, $410a1_4$, and $410a1_5$ of the first coil device $410a1_2$ relative to the central axis of the second portion $410a3_2$.

Figure 17:
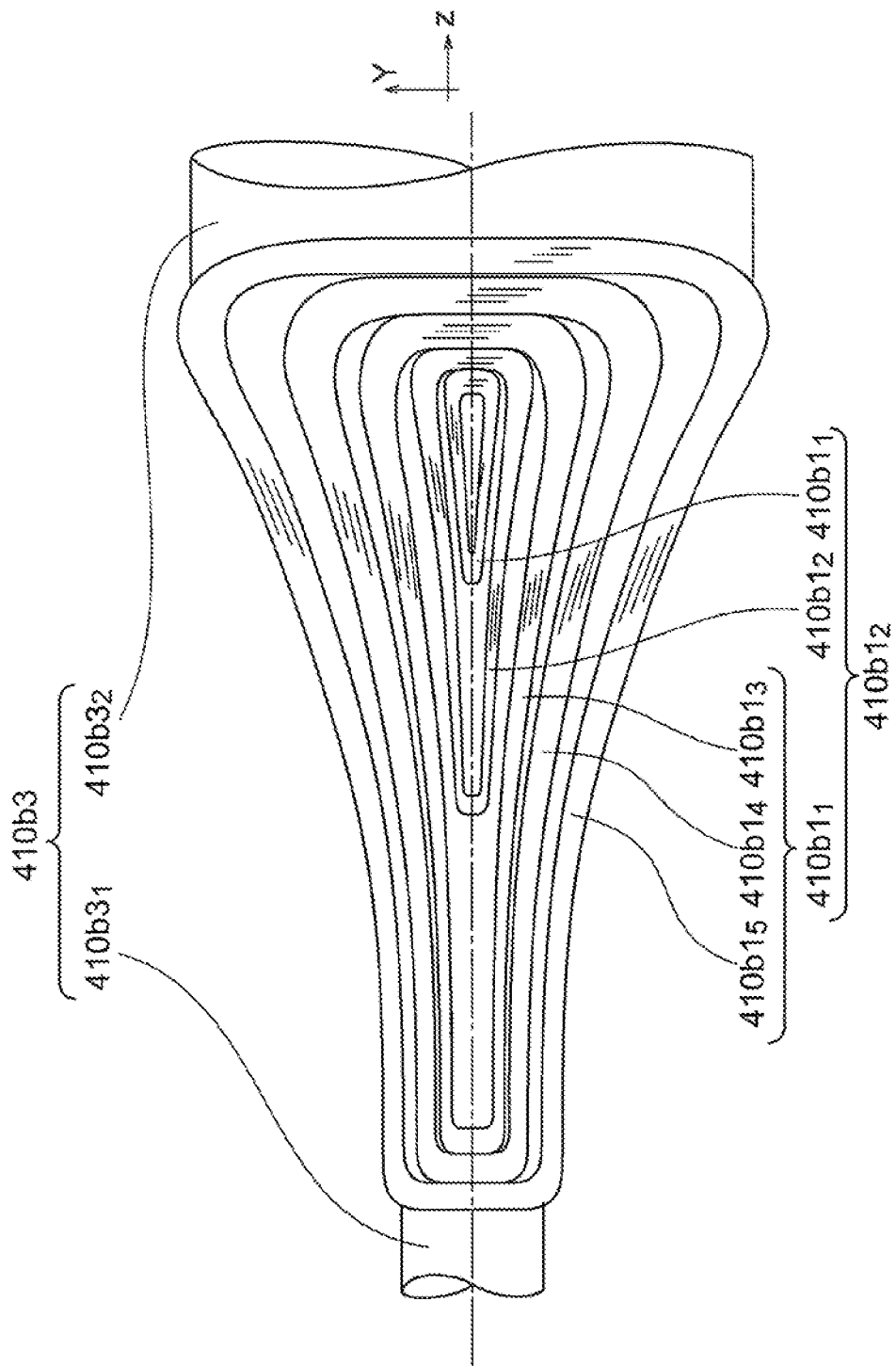
FIG. 17 is an explanatory diagram of a horizontal scanning electromagnet according to the seventh embodiment.

FIG. 17 is a diagram showing the first coil devices $410b1_1$ and $410b1_2$ disposed on one of the side surfaces of the structure $410b3$ at portions corresponding to the horizontal scanning electromagnets $410b_1$ and $410b_2$ in the sixth embodiment. The first coil device $410b1_2$ is disposed on one of the side surfaces of the second portion $410b3_2$, and includes a coil $410b1_{11}$, a coil $410b1_{12}$ disposed outside the coil $410b1_{11}$, a coil $410b1_{13}$ disposed outside the coil $410b1_{12}$, a coil $410b1_{14}$ disposed outside the coil $410b1_{13}$, and a coil $410b1_{15}$ disposed outside the coil $410b1_{14}$. The coil $410b1_{13}$, the coil $410b1_{14}$, and the coil $410a1_{15}$ extend over one of the side surfaces of the first portion $410b3_1$ to form the first coil device $410b1_1$. Although the first coil device $410b1_1$ has three coils in FIG. 17, the number of coils may be one, two, or four or more. Although the first coil device $410b1_2$ has five coils, any number of coils may be disposed if the number is greater than the number of coils of the first coil device $410b1_1$.

The second coil devices (not shown) that make pairs with the first coil devices $410b1_1$ and $410b1_2$ are disposed on the other of the side surfaces of the first portion $410b3_1$ and the second portion $410b3_2$ as in the first embodiment shown in FIGS. 4A, 4B, and 4C. Like the first coil device $410b1_1$ and the first coil device $410b1_2$ shown in FIG. 16, the second coil devices include three coils and five coils, respectively. As in the first embodiment shown in FIGS. 4A, 4B, and 4C, the respective coils of the second coil device disposed on the other of the side surfaces of the first device $410b3_1$ have the same sizes as the coils $410b1_3$, $410b1_4$, and $410b1_5$ of the first coil device $410b1_1$, and are arranged to be symmetrical to the coils $410b1_3$, $410b1_4$, and $410b1_5$ of the first coil device $410b1_1$ relative to the central axis of the first portion $410b3_1$. The respective coils of the second coil device disposed on the other surface of the second portion $410b3_2$ have the same sizes as the coils $410b1_1$, $410b1_2$, $410b1_3$, $410b1_4$, and $410b1_5$ of the first coil device $410b1_2$, and are arranged to be symmetrical to the coils $410b1_1$, $410b1_2$, $410b1_3$, $410b1_4$, and $410b1_5$ of the first coil device $410b1_2$ relative to the central axis of the second portion $410a3_2$.

In the seventh embodiment having the above structure, the intensity of the magnetic field generated by the pair of vertical scanning electromagnets $410a_2$ is greater than the intensity of the magnetic field generated by the pair of vertical scanning electromagnets $410a_1$ if the excitation current having the same value is caused to flow through the pair of vertical scanning electromagnets $410a_1$ and the pair of vertical scanning electromagnets $410a_2$ since the number of coils differs between the pair of vertical scanning electromagnets $410a_1$ and the pair of vertical scanning electromagnets $410a_2$. Therefore, the excitation current may be supplied to the pair of vertical scanning electromagnets $410a_1$ and the pair of vertical scanning electromagnets $410a_2$ by means of the same electromagnet power supply.

Furthermore, since the number of coils differs between the pair of horizontal scanning electromagnets $410b_1$ and the pair of horizontal scanning electromagnets $410b_2$, the intensity of the magnetic field generated by the pair of horizontal scanning electromagnets $410b_2$ is greater than the intensity of the magnetic field generated by the pair of horizontal scanning electromagnets $410b_1$ if the same value of excitation current is caused to flow through the pair of horizontal scanning electromagnets $410b_1$ and the pair of horizontal scanning electromagnets $410b_2$. Therefore, the same electromagnet power supply may be used to supply an excitation current to the pair of horizontal scanning electromagnets $410b_1$ and the pair of horizontal scanning electromagnets $410b_2$.

Like the structure of the fourth embodiment, the above structure of the seventh embodiment is capable of preventing the charged particle beam irradiation apparatus from elongating along the moving direction of the charged particle beam, and suppressing an increase in the aperture to a minimum level. Therefore, a charged particle beam irradiation apparatus that suppresses an increase in size and ensures a sufficient irradiation field may be provided.

Eighth Embodiment

A charged particle beam irradiation apparatus according to an eighth embodiment will be described with reference to FIG. 18. FIG. 18 is a diagram showing a scanning electromagnet 401D included in a charged particle beam irradiation apparatus according to the eighth embodiment. The charged particle beam irradiation apparatus according to the eighth embodiment has a structure in which the scanning electromagnet 401 of the charged particle beam irradiation apparatus 1 according to the first embodiment shown in FIG. 1 is replaced by the scanning electromagnet 401D shown in FIG. 18.

The scanning electromagnet 401D according to the eighth embodiment has a structure obtained by adding a yoke 420 to the outside of the horizontal scanning electromagnets $410b_1$ and $410b_2$ of the scanning electromagnet according to any of the fourth to seventh embodiments. If the aperture of the horizontal scanning electromagnets is smaller than the aperture of the vertical scanning electromagnets, the yoke 420 is disposed outside the vertical scanning electromagnets. FIG. 18 is a cross-sectional view showing the case where the yoke 420 is disposed outside the horizontal scanning electromagnets $410b_1$ and $410b_2$ of the fourth embodiment.

In this embodiment, the aperture of the yoke 420 is shaped to match to the outer shape of the horizontal scanning electromagnets $410b_1$ and $410b_2$. Specifically, the aperture corresponding to the horizontal scanning electromagnet $410b_1$ is substantially constant or increases linearly, and the aperture corresponding to the horizontal scanning electromagnet $410b2$ linearly increases with a rate of change that is different from a rate of change of the horizontal scanning electromagnet $410b_1$. The outer diameter of the yoke 420 is substantially constant. Therefore, the thickness of the yoke 420 is less on the outlet side, from which the charged particle 104c is emitted, than the inlet side.

Figure 19:
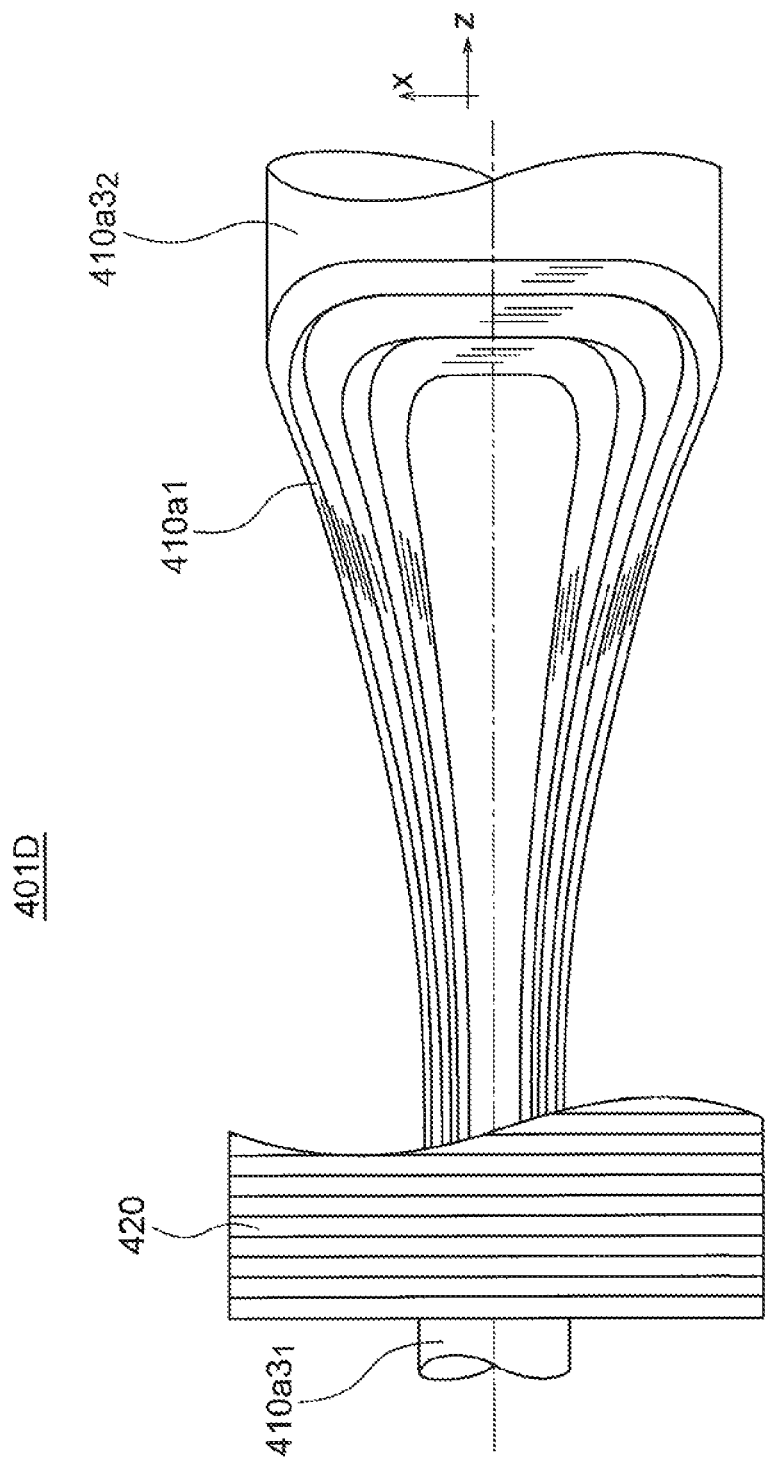
FIG. 19 is a top view of the scanning electromagnet included in the charged particle beam irradiation apparatus according to the eighth embodiment.
Figure 20:
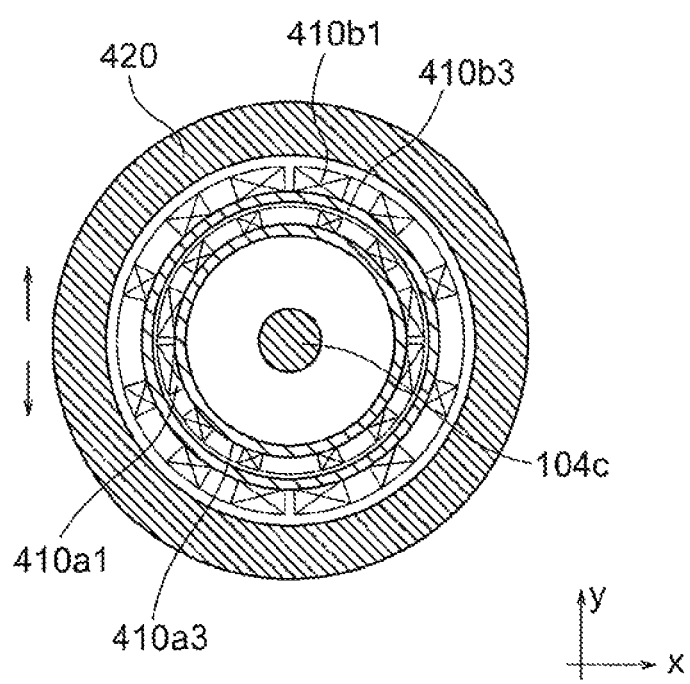
FIG. 20 is a cross-sectional view of the scanning electromagnets included in the charged particle beam irradiation apparatus according to the eighth embodiment.

FIG. 19 is a top view and FIG. 20 is a cross-sectional view of the scanning electromagnet 401D according to this embodiment. FIG. 19 is a cutaway top view of the yoke 420. The length of the yoke 420 is substantially the same as the longitudinal length of the coil device 410a1 of the vertical scanning electromagnet. In FIG. 20, the reference numeral 104c denotes a charged particle beam.

The yoke 420 may be divided into at least two portions. Typically, the yoke 420 is divided into two portions in the Y direction or the X direction. In FIG. 20, the yoke 420 is divided into two in the Y direction as indicated by arrows. This allows easy processing of the inner surface of the yoke 420 and easy assembly of the coils. The inner surface of the yoke 420 is in contact with or close to the outer surface of the coil device 410a1, and formed of a magnetic material such as iron to increase the intensity of the magnetic field and reduce the strayed magnetic field.

Since the scanning electromagnet 401D of this embodiment is driven by an alternating current, the yoke 420 has a structure obtained by arranging thin iron sheets such as magnetic steel sheets in the longitudinal direction, and bonding the sheets with a resin. This reduces heat generated by the yoke 420, and error in magnetic field caused by eddy current.

As described above, the inner surface of the yoke 420 is in contact with or close to the outer surface of the coil device 410a1. However, the outer surface of the yoke 420 is unchanged and the outside diameter is constant. Such a shape of the yoke 420 efficiently provides effects to improve the magnetic field strength of the yoke 420 and to produce the yoke 420 easily since the yoke 420 is thicker at a portion where the aperture is preferably small and the magnetic field strength is strong, and is thinner at a portion where the aperture is large and the magnetic field strength is weak.

Like the structure of the fourth embodiment, the above structure of the eighth embodiment is capable of preventing the charged particle beam irradiation apparatus from elongating along the moving direction of the charged particle beam, and suppressing an increase in the aperture to a minimum level. Therefore, a charged particle beam irradiation apparatus that suppresses an increase in size, and ensures a sufficient irradiation field may be provided. Furthermore, the presence of the yoke 420 prevents the magnetic field from leaking to the outside.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A charged particle beam irradiation apparatus comprising:
a first scanning electromagnet device configured to deflect a charged particle beam to a first direction that is substantially perpendicular to a second direction along which the charged particle beam enters, the first scanning electromagnet device having an aperture on an outlet side larger than that on an inlet side; and
a second scanning electromagnet device configured to deflect the charged particle beam to a third direction that is substantially perpendicular to a plane including the first direction and the second direction, the second scanning electromagnet device having an aperture on an outlet side larger than that on an inlet side,
the first scanning electromagnet device and the second scanning electromagnet device being disposed to be substantially equally distant from a plane to which the charged particle beam is irradiated.

2. The apparatus according to claim 1, wherein:
the first scanning electromagnet device includes a first structure that is hollow, a first coil disposed on a first surface of the first structure, and a second coil disposed on a second surface of the first structure, the first surface and the second surface being opposed to each other in the first direction; and
the second scanning electromagnet device includes a second structure that is hollow, the second structure covering the first structure, the first coil, and the second coil, a third coil disposed on a third surface of the second structure, and a fourth coil disposed on a fourth surface of the second structure, the third surface and the fourth surface being opposed to each other in the third direction,
the first scanning electromagnetic device and the second scanning electromagnetic device being located at the same position in the second direction, and the second scanning electromagnetic device being located outside of the first scanning electromagnetic device in a plane including the first direction and the third direction.

3. The apparatus according to claim 1, wherein:
the first scanning electromagnet device includes a plurality of first scanning electromagnets arranged along the second direction;
the second scanning electromagnet device includes a plurality of second scanning electromagnets arranged along the second direction so as to correspond to the first scanning electromagnets;
the first scanning electromagnets together with the corresponding second scanning electromagnets are arranged in parallel with the second direction; and
an aperture formed by the first scanning electromagnets and the second scanning electromagnets increases from an inlet side, at which the charged particle beam enters, to an outlet side at which the charged particle beam exits.

4. The apparatus according to claim 3, wherein:
each of the first scanning electromagnets includes a first structure that is hollow, a first coil disposed on a first surface of the first structure and a second coil disposed on a second surface of the first structure, the first coil and the second coil being opposed to each other in the first direction; and
each of the second scanning electromagnets includes a second structure that is hollow and covers the first structure, the first coil, and the second coil, a third coil disposed on a third surface of the second structure, and a fourth coil disposed on a fourth surface of the second structure, the third surface and the fourth surface being opposed to each other in the third direction, each of the first scanning electromagnets being located inside of corresponding one of the second scanning electromagnets in a plane including the first direction and the third direction.

5. The apparatus according to claim 1, wherein an aperture formed by the first scanning electromagnet device and the second scanning electromagnet device increases from an inlet side, at which the charged particle beam enters, along the second direction.

6. The apparatus according to claim 5, wherein:
the first scanning electromagnet device includes a first structure that is hollow with an aperture sequentially increasing from an inlet side, at which the charged particle beam enters, along the second direction, a first coil disposed on a first surface of the first structure, and a second coil disposed on a second surface of the first structure, the first surface and the second surface being opposed to each other in the first direction; and
the second scanning electromagnet device includes a second structure that is hollow with an aperture sequentially increasing along the second direction from an inlet side, at which the charged particle beam enters, the second structure covering the first structure, the first coil, and the second coil, a third coil disposed on a third surface of the second structure, and a fourth coil disposed on a fourth surface of the second structure, the third surface and the fourth surface being opposed to each other in the third direction.

7. The apparatus according to claim 1, further comprising a yoke, which is hollow, disposed outside the first scanning electromagnet device and the second scanning electromagnet device.

8. The apparatus according to claim 1, wherein:
the first scanning electromagnet device includes a first scanning electromagnet with an aperture that is substantially constant or increases linearly from an inlet side to which the charge particle beam enters to an outlet side from which the charged particle beam exits, and a second scanning electromagnet disposed after the first scanning electromagnet, the second scanning electromagnet having an aperture increasing from an inlet side to an outlet side, the aperture on the outlet side of the first scanning electromagnet being substantially equal to the aperture on the inlet side of the second scanning electromagnet; and
the second scanning electromagnet device includes a third scanning electromagnet with an aperture that is substantially constant or increases linearly from an inlet side to which the charge particle beam enters to an outlet side from which the charged particle beam exits, and a fourth scanning electromagnet disposed after the third scanning electromagnet, the fourth scanning electromagnet having an aperture increasing linearly from an inlet side to the outlet side, the aperture on the outlet side of the third scanning electromagnet being substantially equal to the aperture on the inlet side of the fourth scanning electromagnet.

9. The apparatus according to claim 8, wherein:
the first scanning electromagnet and the second scanning electromagnet include a first structure that is hollow, a first coil device disposed on a first surface of the first structure, and a second coil device disposed on a second surface of the first structure, the first surface and the second surface being opposed to each other in the first direction;
the third scanning electromagnet and the fourth scanning electromagnet include a second structure that is hollow and covers the first structure, the first coil device, and the second coil device, a third coil device disposed on a third surface of the second structure, and a fourth coil device disposed on a fourth surface of the second structure, the third surface and the fourth surface being opposed to each other in the third direction;
the first structure includes a first portion with an aperture being substantially the same on an inlet side and an outlet side or increasing linearly, and a second portion connecting to the first portion and having an aperture increasing linearly toward the outlet side; and
the second structure includes a third portion with an aperture being substantially the same on an inlet side and an outlet side or increasing linearly, and a fourth portion connecting to the third portion and having an aperture increasing linearly toward the outlet side.

10. The apparatus according to claim 9, wherein:
the first coil device includes a first coil disposed over the first portion and the second portion of the first structure;
the second coil device includes a second coil disposed over the first portion and the second portion of the first structure;
the third coil device includes a third coil disposed over the third portion and the fourth portion of the second structure; and
the fourth coil device includes a fourth coil disposed over the third portion and the fourth portion of the second structure.

11. The apparatus according to claim 9, wherein:
windings of the first coil are more in the second portion than the first portion;
windings of the second coil are more in the second portion than the first portion;
windings of the third coil are more in the fourth portion than the third portion; and
windings of the fourth coil are more in the fourth portion than the third portion.

12. The apparatus according to claim 9, wherein:
the first coil device includes a first coil disposed on the first portion of the first structure, and a second coil disposed on the second portion of the first structure;
the second coil device includes a third coil disposed on the first portion of the first structure, and a fourth coil disposed on the second portion of the first structure;
the third coil device includes a fifth coil disposed on the third portion of the second structure, and a sixth coil disposed on the fourth portion of the second structure; and
the fourth coil device includes a seventh coil disposed on the third portion of the second structure, and an eighth coil disposed on the fourth portion of the second structure.

13. The apparatus according to claim 12, wherein:
windings of the second coil are more than windings of the first coil, windings of the fourth coil are more than windings of the third coil, windings of the sixth coil are more than windings of the fifth coil, and windings of the eighth coil are more than windings of the seventh coil.

14. The apparatus according to claim 8, further comprising a yoke, which is hollow, disposed outside the first scanning electromagnet device and the second scanning electromagnet device.

15. The apparatus according to claim 14, wherein the yoke has an aperture shaped along an outer portion of the first scanning electromagnet device or the second scanning electromagnet device having a larger aperture.

16. The apparatus according to claim 14, wherein the yoke has a thickness less on an outlet side, from which the charged particle beam exits, than an inlet side, from which the charged particle beam enters.

17. The apparatus according to claim 14, wherein the yoke has a structure obtained by arranging iron sheets along the second direction.

18. The apparatus according to claim 2, wherein each of the first to fourth coils has a saddle-like shape.

19. The apparatus according to claim 2, further comprising a yoke, which is hollow, disposed outside the first scanning electromagnet device and the second scanning electromagnet device.

20. The apparatus according to claim 4, wherein the first to fourth coils have a saddle-like shape.

* * * * *